United States Patent
Corbett et al.

(10) Patent No.: US 10,365,198 B2
(45) Date of Patent: Jul. 30, 2019

(54) PARTICLE CHARACTERIZATION

(71) Applicant: Malvern Panalytical Limited, Malvern (GB)

(72) Inventors: Jason Cecil William Corbett, Malvern (GB); David Bryce, Malvern (GB)

(73) Assignee: Malvern Panalytical Limited, Malvern Worcestershire (GB)

( * ) Notice: Subject to any disclaimer, the term of this patent is extended or adjusted under 35 U.S.C. 154(b) by 0 days.

(21) Appl. No.: 15/454,814

(22) Filed: Mar. 9, 2017

(65) Prior Publication Data

US 2017/0307495 A1    Oct. 26, 2017

(30) Foreign Application Priority Data

Apr. 21, 2016 (GB) .................................. 1606918.9

(51) Int. Cl.
*G01N 15/02* (2006.01)
*G01N 15/00* (2006.01)

(52) U.S. Cl.
CPC . *G01N 15/0211* (2013.01); *G01N 2015/0222* (2013.01); *G01N 2015/03* (2013.01)

(58) Field of Classification Search
CPC .......... G01N 21/88; G01N 2021/4707; G01N 2021/4711; G01N 2021/4792; G01N 2021/556; G01N 2021/8809; G01N 2021/8848; G01N 2021/8864; G01N 2021/8877; G01N 2021/8896; G01N 21/21; G01N 21/47

See application file for complete search history.

(56) References Cited

U.S. PATENT DOCUMENTS

| | | | | |
|---|---|---|---|---|
| 4,273,443 A | * | 6/1981 | Hogg | G01N 15/1436 250/574 |
| 4,690,561 A | * | 9/1987 | Ito | G01N 15/1434 250/201.1 |
| 6,178,346 B1 | * | 1/2001 | Amundson | A61B 5/0086 348/77 |
| 2009/0180120 A1 | * | 7/2009 | Kanayama | G01N 21/255 356/440 |
| 2010/0020312 A1 | * | 1/2010 | Jeong | G01J 3/02 356/73 |

(Continued)

FOREIGN PATENT DOCUMENTS

DE    202016006846    2/2017
EP    2 721 399    4/2014

(Continued)

OTHER PUBLICATIONS

Optotune located at www.optotune.com/publications-2, visited on Mar. 29, 2017; 2 pages.

(Continued)

*Primary Examiner* — Michael P Stafira
(74) *Attorney, Agent, or Firm* — Morrison & Foerster LLP

(57) ABSTRACT

A particle characterization apparatus comprising: a light source for illuminating a sample with a light beam; a detector arranged to detect scattered light from the interaction of the light beam with the sample; and a focus tuneable lens arranged to collect the scattered light for the detector from a scattering volume and/or to direct the light beam into the sample.

18 Claims, 13 Drawing Sheets

(56) References Cited

U.S. PATENT DOCUMENTS

| | | | |
|---|---|---|---|
| 2013/0320216 A1* | 12/2013 | Aiko | G01B 11/303 |
| | | | 250/349 |
| 2014/0152986 A1 | 6/2014 | Trainer | |
| 2015/0115174 A1 | 4/2015 | Chen | |
| 2016/0146732 A1* | 5/2016 | Freitag | G01N 15/1434 |
| | | | 356/338 |
| 2016/0202164 A1* | 7/2016 | Trainer | G01N 15/0211 |
| | | | 356/336 |
| 2016/0290912 A1* | 10/2016 | Kent | G06K 9/00134 |
| 2017/0234788 A1* | 8/2017 | Di Carlo | G01N 15/1404 |
| | | | 356/36 |
| 2017/0248510 A1* | 8/2017 | Pedrono | G01N 15/1436 |

FOREIGN PATENT DOCUMENTS

| | | |
|---|---|---|
| WO | WO 2012/172330 A1 | 12/2012 |
| WO | 2016/034902 | 3/2016 |

OTHER PUBLICATIONS

International Search Report and Written Opinion dated Jan. 25, 2018, directed to International Application No. PCT/GB2017/053204; 14 pages.

\* cited by examiner

PARTICLE CHARACTERIZATION

CROSS-REFERENCE TO RELATED APPLICATIONS

This application claims priority to Great Britain Patent Application No. 1606918.9, filed on Apr. 21, 2016, the contents of which prior application is incorporated herein by reference.

FIELD OF THE INVENTION

The present invention relates to a method and apparatus for particle characterization.

BACKGROUND OF THE INVENTION

Photon correlation spectroscopy (or dynamic light scattering, DLS) measures the time resolved signal scattered from particle suspensions. The relaxation time of the sample is determined using the correlation function of the scattered signal, from which the particle size distribution can be estimated. The technique works best when each particle in suspension scatters light from the illuminating light beam (e.g. laser) only and not light that has already been scattered from other particles. At high concentrations multiple scattering tends to degrade the technique.

Within a small range of backscattered angles, multiply scattered signals may have an almost identical relaxation time (from which the particle size is calculated) to the singly scattered signal.

An existing technique (which may be termed non-invasive back scatter, or NIBS) uses a moving lens to place an illuminating laser optical path and a backscatter detection optical path into a variable position within a sample cuvette, as shown in FIGS. 1 and 2. The intersection of the illuminating optical path and the detection optical path may be termed the detection region or scattering volume.

When the sample is turbid (i.e. has a high concentration of particles), the detection region can be placed near to the cell wall, which significantly reduces multiple scattering due to the foreshortened illumination path length within the sample. In addition, a backscatter angle may be selected at which multiply scattered signals have a similar relaxation time to singly scattered signals, as already described.

Moving the detection region within the cell is advantageous, and it is also advantageous to maintain a selected angle of detection throughout the range of movement, so as to combine both benefits mentioned above.

At low particle concentration, the detection region may be moved toward the cell centre, or at least away from the static scattering contribution from the wall. Whilst the static scattering contribution from the wall may be negligible compared with the scattering contribution from particles in a high concentration sample, such static scattering from the wall may be a source of uncorrelated noise (or even static reference signal), for low concentration samples. The static scattering contribution from the wall may therefore decrease signal to noise ratio. The static scattering increases the correlogram baseline and thence reduces its intercept, which is a measure of the signal-to-noise of the measurement. Moving the detection region away from the cell wall may therefore improve the signal to noise ratio.

In the low sample concentration limit, DLS suffers from number fluctuations, whereby the scattered signal varies because of the fluctuation in the number of particles within the detection region, in addition to the contribution to the scattering from the Brownian motion of the particles. However, it may not be practical to simply expand the size of the detection beam to accommodate more particles, because this may increase the size of the beam out of a single coherence area. The highest signal-to-noise measurements using DLS may rely on measurement from within a single coherence area.

The signal to noise ratio of the correlogram is generally interpreted from the intercept of the correlogram and the y-axis. In order to maximize this value a single mode fibre may be used in the detection optical path, to select out a single spatial frequency from the 'image' of the speckle field. Simply increasing the size of the detection optical path may result in non-optimal coupling into such a fibre or may collect light from more than one coherence area, which may reduce the signal to noise ratio.

A method and apparatus for solving or ameliorating at least some of the above mentioned problems is desirable.

SUMMARY OF THE INVENTION

According to a first aspect of the invention, there is provided a particle characterization apparatus comprising: a light source for illuminating a sample with a light beam; a detector arranged to detect scattered light from the interaction of the light beam with the sample; and a focus tuneable lens arranged to collect the scattered light for the detector from a scattering volume and/or to direct the light beam into the sample.

The terms "scattering volume" and "detection region" are synonymous in this disclosure.

Adjusting the focus tuneable lens may adjust a location of the scattering volume, to focus the detector on a scattering volume coincident with the light beam. In some embodiments, the location of the scattering volume may be adjustable without translating a lens or lens element, which may make the apparatus more reliable, and/or may allow for faster adjustment of the illumination and/or detection optical path.

The apparatus may be arranged so that adjustment of the focal length of the focus tuneable lens results in a change in the location of the scattering volume without a change in the angle between the illumination and detection optical paths.

The apparatus may comprise a sample cell, and/or a sample cell holder, for receiving the sample (e.g. in the sample cell).

The apparatus may comprise a detection optical path, by which the scattered light reaches the detector, and an illumination optical path, by which the light beam reaches the sample from the light source. Both the detection optical path and the illumination optical path may pass through the focus tuneable lens. In some embodiments only the detection optical path or only the detection optical path may pass through the focus tuneable lens.

The focus tuneable lens may have an optical axis. The detection optical path may be at a first (non-zero) angle to the optical axis. The illumination optical path may be at a second (non-zero) angle to the optical axis. The first angle and second angle may be substantially equal.

The first angle and/or second angle may be between 5 degrees and 15 degrees, and/or may 10 degrees or less or 5 degrees or less. The angle between the detection and illumination optical path at the scattering volume may be 10 degrees or less.

The illumination and detection optical path may lie in a common plane (or may not be in a common plane). The common plane may be horizontal or vertical (an opening of a sample cell may face upwards in an instrument, for obvious reasons).

The detection optical path and the illumination optical path may cross at a first location at a distance from the focus tuneable lens. The first location may be on the optical axis of the focus tuneable lens. The focus tuneable lens may be operable to have a focal length that co-locates a focal point of the focus tuneable lens with the first location.

The focus tuneable lens may be un-powered (or at a centre of an operating range of focal lengths) when the focal point is co-located with the first location. This may be advantageous because the focus tuneable lens may have more stability or linearity at or near a quiescent or central operating point.

A light source lens may be arranged on the illumination optical path between the light source and the focus tuneable lens. A detector lens may be arranged on the detection optical path between the detector and the focus tuneable lens. The light source lens may be arranged to focus the illumination optical path on a principal plane of the focus tuneable lens. The detector lens may be configured to focus the detection optical path on a principle plane (e.g. the same principle plane) of the focus tuneable lens.

A focussing lens may be provided between the focus tuneable lens and the sample (e.g. along the illumination and/or detection optical path). The focussing lens may comprise at least one fixed focal length lens.

The focussing lens may have a focal point on a principle plane of the focus tuneable lens. The focussing lens may have a further focal point within the sample cell (or sample). This arrangement means that the focussing lens images the scattering volume at the focus tuneable lens.

The apparatus may be configured such that moving the position of the scattering volume in the sample closer to the light source by changing the focal length of the focus tuneable lens results in a decrease in the scattering volume. Moving the position of the scattering volume in the sample further from the light source by changing the focal length of the focus tuneable lens may result in an increase in the scattering volume The detection optical path and illumination optical path may be focussed within the sample cell, or may be collimated within the sample cell, or may be between these conditions (e.g. with convergent illumination and detection paths within the sample cell but not coming to focus within the sample cell).

An illumination mirror may be provided between the focus tuneable lens and the sample, for directing the illumination optical path into the sample cell, and the illumination optical path may be arranged so as not to pass through the focus tuneable lens. The illumination mirror may direct the illumination optical path along an axis of the focus tuneable lens into the sample. This arrangement may make optical alignment more straightforward, because more optical components are aligned on a common axis, rather than at angles to each other.

The apparatus may further comprise a focussing reflector configured to direct at least one of the illumination path and detection path into the sample.

The focussing reflector may be configured to direct the illumination optical path and detection optical path into the sample. The apparatus may be configured so that varying the focal length of the focus tuneable lens changes the angle of intersection of the illumination and detection optical path within the sample without altering the position and/or size of the scattering volume.

The apparatus may further comprise a beam splitter configured to direct some of the illuminating light beam onto the reflector to mix with the scattered light from the detection optical path. This enables heterodyne optical detection at the detector.

The beam splitter may conveniently be positioned at a point of intersection of the illumination optical path and detection optical path.

The apparatus may further comprise an actuator for moving/vibrating at least one optical element in the illumination optical path and/or detection optical path, so as to facilitate modulated heterodyne optical detection (by spatial light modulation of the illumination and/or detection optical path).

The apparatus may be configured to perform a zeta potential measurement.

The detection optical path may comprise a planar reflector, and an actuator may be configured to move the planar reflector substantially normal to the plane of the reflector so as to spatially modulate the detection optical path.

The apparatus may comprise a sample holder with an opposed pair of electrodes, the sample holder configured to hold a sample in position in a measurement volume between the pair of electrodes such that a planar surface of the sample is aligned orthogonally to the electrode surfaces, the planar surface adjacent to the scattering volume, wherein adjustment of the focus tuneable lens results in adjustment of the relative position of the planar surface and the scattering volume by moving the scattering volume (e.g. while the planar surface remains static). This adjustment may occur without translating the light source, and/or without translating any optical elements in the illumination or detection optical path.

The focus tuneable lens may be operable to compensate for at least one of: a refractive index of the sample, an orientation of a sample cell within which the sample is held, a refractive index of the sample cell and the geometry of the sample cell.

The focus tuneable lens may be mounted on a translation stage.

The focus tuneable lens may comprise a deformable lens. The focus tuneable lens may comprise a material in which a refractive index may be varied by application of a stimulus. The focus tuneable lens may comprise an optical sub-assembly comprising more than one lens element, with at least one of the more than one lens element being moveable.

The focus tuneable lens may be arranged to collect at least one of forward scattered light, back scattered light and side scattered light.

Forward scattered light may be defined as scattered light with a propagation direction having a component in the direction of propagation of the light beam. Back scattered light may be defined as scattered light with a propagation direction having a component in a direction opposite to the direction of propagation of the light beam. Side scattered may be defined as scattered light that propagates in a direction that is substantially perpendicular to the direction of propagation of the light beam.

The light beam may pass through the focus tuneable lens.

According a second aspect of the invention, there is provided a particle characterization apparatus comprising: a sample cell for holding a sample, a light source for producing a light beam for illuminating the sample in the sample cell, thereby producing scattered light (e.g. backscattered light) by the interaction of the light beam with the sample; a focussing lens for focussing the light beam within the sample; and a detector for detecting the scattered light along a detection optical path that intersects the focussed light beam within the sample, the intersection of the focussed light beam and the detection optical path in the sample defining a detection region; wherein the apparatus comprises an optical arrangement for varying the volume of the detection region.

The optical arrangement for varying the volume of the detection region may comprise a focus tuneable lens as described with reference to the first aspect, in combination with any of the other features of the first aspect.

The apparatus may be configured to allow the position of the detection region within the sample to be varied. For turbid samples the detection region may be located near a sample cell wall and a small detection region used (by adjusting the beam width incident on the focussing lens to be relatively large). For samples with a low particle concentration, the detection region may be located remote from the sample cell wall, and a relatively large detection region used.

In some embodiments, the ability to adjust the volume of the detection region allows the measurement parameters of the particle characterisation process to be better optimized to the properties of the sample, thereby improving signal to noise ratio for samples with high and/or low particle concentrations. Adjustment of both the location and volume of the detection region facilitates improved optimisation of the measurement parameters, and enables significant improvements in the lowest and/or highest concentration of particles that can reliably be characterized.

The optical arrangement for varying the volume of the detection region may be operable to vary the light beam width incident on the focussing lens.

The optical arrangement for varying the light beam width incident on the focussing lens may comprise a beam expander.

The beam expander may comprise a moveable lens, operable to vary the light beam width incident on the focussing lens with movement of the moveable lens.

The term "moveable lens" may refer to a lens mounted on a translation arrangement (or stage) for controllably repositioning the lens (for example, by rotating a lead screw).

The beam expander may further comprise a fixed lens between the light source and the moveable (or focus tuneable) lens.

The beam expander may be operable to produce a collimated output beam of variable width (e.g. from a collimated input beam, although this is not essential).

The fixed lens may comprise a diverging lens or a converging lens.

The moveable lens (or focus tuneable lens) may comprise a converging lens.

The focussing lens may focus the detection optical path within the sample.

The focussing lens may be moveable, so as to vary a location of a focal plane of the light beam in the sample with movement of the focussing lens.

Moving the focussing lens may also vary the location of a focal plane of the detection optical path, thereby varying the position of the detection region within the sample with movement of the focussing lens.

The optical arrangement for varying the light beam width incident on the focussing lens may comprise: a converging lens between the focussing lens and light source causing the light beam to be convergent at the focussing lens, and an actuator operable to move the focussing lens so as to vary the distance between the focussing lens and the converging lens.

The converging lens (of the optical arrangement) may be a fixed lens.

The detection optical path may comprise an optical fibre.

The optical fibre may comprise a single mode fibre.

The apparatus may further comprise a coupling lens arranged to couple the detection optical path to the optical fibre.

The coupling lens may comprise a graded refractive index lens.

The focussing lens may comprise a focus tuneable lens.

The apparatus may be operable to perform a dynamic light scattering measurement using an output from the detector.

The apparatus may comprise a processor for performing the dynamic light scattering measurement. Performing a dynamic light scattering experiment may comprise performing a correlation operation on a time series of scattering intensity data obtained from the detector, and then processing the resulting correlogram to determine at least one of an average particle size ($Z_{average}$) a polydispersity index (pdi) and a particle size distribution. Processing the correlogram may comprise using the well know cumulants technique, or may involve some other technique such as CONTIN, or non-negative least squares.

According to a third aspect, there is provided a method of performing a dynamic light scattering measurement, comprising:
  adjusting a location and a volume of a detection region in a sample cell in response to a concentration of particles within a sample held by the sample cell;
  illuminating the sample with a light beam, thereby producing scattered light by the interaction of the light beam with the sample;
  detecting scattered light along a detection optical path that intersects the light beam within the sample at the detection region;
  deriving characteristics of particles within the sample from the detected scattered light by performing a dynamic light scattering analysis.

Adjusting the location and volume of the detection region may comprise moving the detection region closer to a wall of the sample cell through which the illumination light beam passes to illuminate the sample and reducing the volume of the detection region.

The adjusting may be in response to a concentration of particles that is greater than a first predetermined threshold (which may be determined from a previous step of deriving characteristics by DLS).

Adjusting the location and volume of the detection region may comprise moving the detection region further from a wall of the sample cell through which the illumination light beam passes to illuminate the sample, and increasing the volume of the detection region.

The adjusting may be in response to a concentration of particles that is lower than a second predetermined threshold.

According to a fourth aspect, there is provided a method of performing a dynamic or static light scattering measurement, comprising:
  illuminating the sample with a light beam, thereby producing scattered light by the interaction of the light beam with the sample;
  detecting scattered light along a detection optical path that intersects the light beam within the sample at a detection region, thereby obtaining data;
  adjusting at least one of a location of the detection region, a volume of the detection region, or an angle between the illumination and detection optical path at the detection region, by changing the focal length of a focus tuneable lens in at least one of the illumination and detection optical path;

repeating, at least once, the step of detecting scattered light after performing at least one corresponding step of adjustment by changing the focal length of the focus tuneable lens;

performing a static or dynamic light scattering measurement using the data obtained from at least one focal length of the focus tuneable lens.

The method may comprise performing a dynamic light scattering measurement in which each adjusting step changes at least a position of the detection region, and each adjusting step is in response to measurement data corresponding with a preceding adjustment step. This approach may be used to determine an optimal measurement location for a dynamic light scattering measurement—for a turbid sample the optimal location may be near to the sample cell wall, and for a low concentration sample the optimal location may be near to the centre of the sample cell. The average count rate of the measurement data is one way to determine an appropriate measurement location. The intercept of a correlogram produced from the measurement data may alternative or additionally be used to determine an appropriate measurement location.

The method may comprise performing a dynamic or static light scattering measurement by obtaining measurement data from a plurality of scattering angles by adjusting the focal length of the focus tuneable lens. Multi-angle static light scattering measurements and dynamic light scattering measurement are well known in the art of particle characterisation, but these are normally obtained by physically translating optical components (e.g. the light source), or by using multiple detectors at different angles. Using a focus tuneable lens to select different measurement angles enables a faster adjustment time, and may reduce costs and simplify construction (e.g. by avoiding a translation stage and/or multiple detectors at different angles).

The method may further comprise providing an estimated concentration of particles within the sample cell.

The estimated concentration may comprise a qualitative indicator of concentration.

The method may further comprise measuring the concentration of particles within the sample.

Features of any aspect may be combined with features of any other aspect, and vice versa. The method of any aspect or embodiment may be performed with an apparatus of the first or second aspect, in accordance with the features thereof.

Any aspect that includes a focus tuneable lens may alternatively be implemented with a moving lens arrangement. For example, the focus tuneable lens mentioned in the fourth aspect may be replaced with a moveable lens (i.e. a lens and translation stage), similar to that described in relation to the second aspect.

BRIEF DESCRIPTION OF THE DRAWINGS

Embodiments of the invention will now be described, with reference to the accompanying drawings, in which.

DETAILED DESCRIPTION OF THE INVENTION

Figure 1:
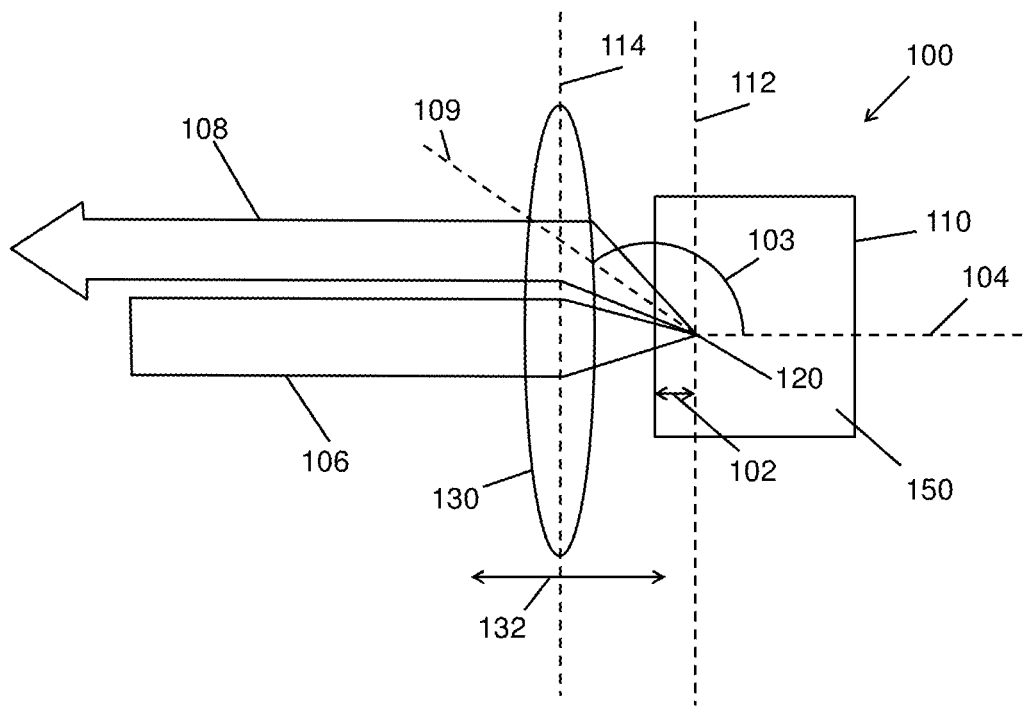
FIG. 1 is a schematic diagram of a prior art NIBS arrangement with the detection region in a first position.
Figure 2:
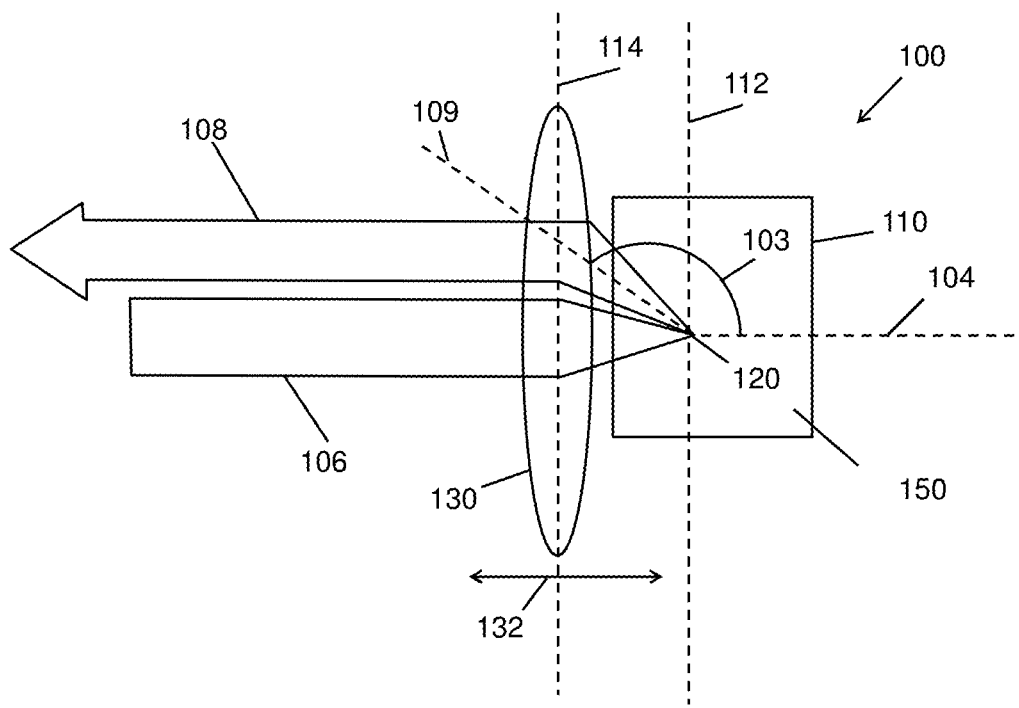
FIG. 2 is a schematic diagram of a prior art NIBS arrangement with the detection region in a second position.

Referring to FIGS. 1 and 2, a prior art NIBS arrangement 100 is shown, in which an illumination beam 106 is focussed on a sample 150 within a sample cell 110 by a focussing lens 130.

A detection optical path 108 receives light scattered from the illumination beam 106 by particles dispersed within the sample 150. The detection optical path 108 defines the field of view of a detector (not shown) for detecting the scattered light. The detection optical path 108 may receive light scattered at a narrow range of angles, centred on a specific scattering angle 103 along detection axis 109. The detection optical path 108 is also focussed within the sample 150 by the focussing lens 130.

The intersection of the illumination beam 106 and the detection optical path 108 define a detection region 120. The position of the detection region 120 within the sample cell 110 can be varied by moving the focussing lens 130, which varies the position of a focal plane 112 of the focussing lens 130 within the sample cell 110. As the focussing lens moves closer to the sample cell, the detection volume moves in the same direction, increasing a distance 102 between the detection region 120 and a cell wall through which the light beam 106 passes to illuminate the sample 150. In FIG. 1 the detection volume 120 is positioned closer to this wall of the sample cell 110 than is the case in FIG. 2.

As discussed above, this arrangement provides for adjustment of the position of the detection region 120, but does not enable adjustment of the volume of the detection region 120.

Figure 3:
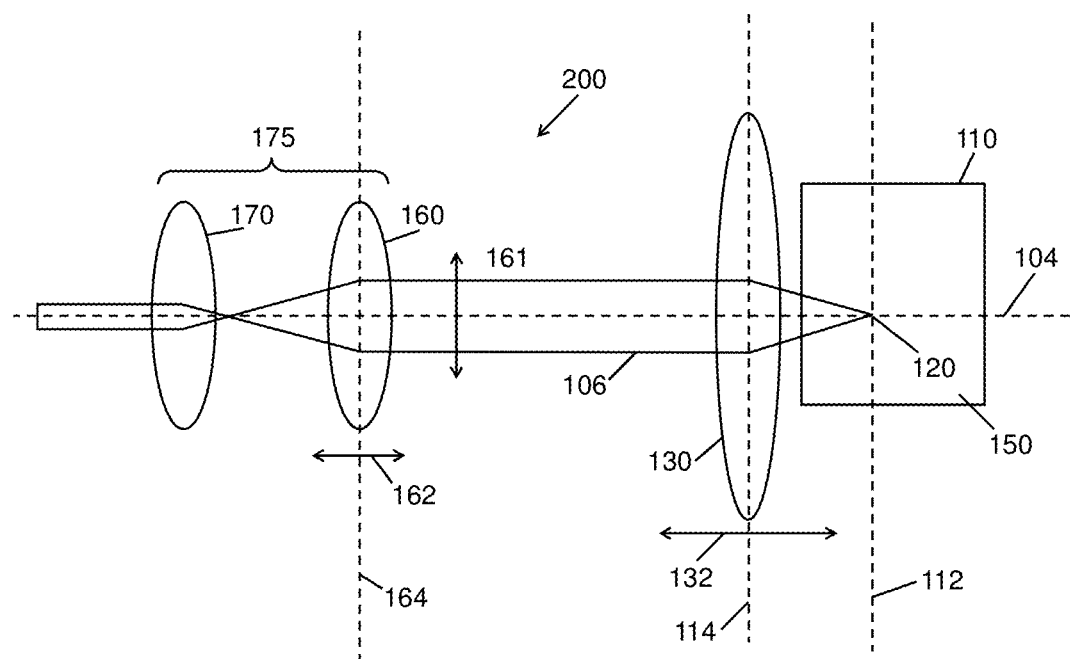
FIG. 3 is a schematic diagram of an illumination optical path in accordance with an embodiment in which a moveable lens is configured to vary the width of an illumination beam that is incident on the focussing lens.

Referring to FIG. 3, an illumination optical path 200 is shown comprising a beam expander 175, focussing lens 130 and sample cell 110. The beam expander 175 is arranged to receive an illuminating light beam 106 from a light source (not shown), and to vary the width 161 of the illuminating light beam 106 incident on the focussing lens 130. The illuminating light beam 106 defines a light beam axis 104.

The beam expander 175 in this embodiment comprises a fixed lens 170 and a moveable lens 160. The fixed lens 170 is disposed between the light source and the moveable lens 160, and is a converging lens. The moveable lens 160 is moveable along the light beam axis 104. The range of movement of the moveable lens 160 may occupy a position on the light beam axis that is after a focal plane of the fixed lens 170, so that the light beam 106 incident on the moveable lens 160 is diverging.

The moveable lens 160 may be configured to collimate the diverging light beam 106 following the focal plane of the fixed lens 170, so that the beam expander 175 produces a collimated beam of light 106 of variable beam width (or diameter) 161 incident on the focussing lens 130.

There is a Fourier relationship between the plane 114 of the focussing lens 130 and the plane 164 of the moveable lens 160, such that an increased beam diameter 161 incident on the focussing lens 130 results in a tighter waist of focus within the focal plane 112 within the sample 150. Conversely, a narrower beam diameter 161 incident on the focussing lens 130 results in a broader waist of focus within the focal plane 112 within the sample 150. A narrower waist of focus equates to a smaller detection region 120, and broader waist equates to a larger detection region 120.

Figure 5:
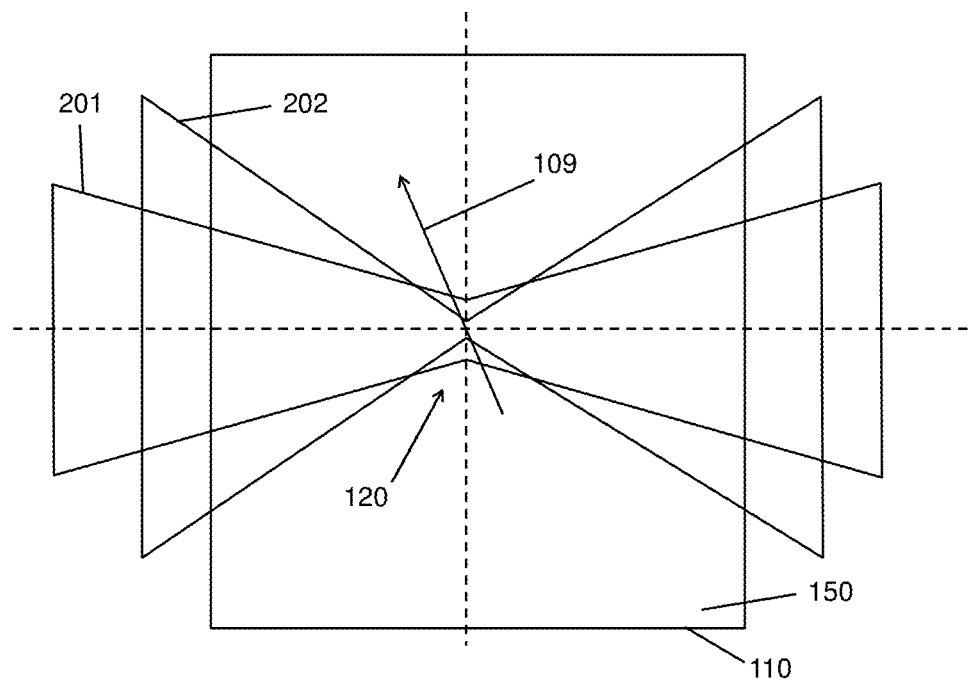
FIG. 5 is a schematic diagram of the detection region illustrating a beam waist for two different beam widths at the focusing lens.

FIG. 5 illustrates the relationship between the width of the beam at the focussing lens 130 and the size of the detection region 120. The path of a beam 201 that is narrow at the focussing lens 130 is compared with the path of a beam 202 that is broader at the focussing lens 130. It can be seen that the detection axis 109 intersects with a longer illuminated region of the sample for the bream 201 than for the beam 202. It will be appreciate that the detection optical path is not confined to the axis 109, but the relationship is nevertheless clear.

Moving the moveable lens 160 further from the fixed lens 170 results in a larger beam diameter 161, which provides a narrower beam waist at the focal plane 112 of the focussing lens 130, within the sample 150. Such a narrow beam waist is particularly suitable for characterization of turbid samples 150 with high concentration of particles. A detection region 120 with a smaller volume may be positioned closer to a wall of the sample cell 110, reducing the probability of multiple scattering, which directly results in an increase in the maximum particle concentration that can be reliably characterized by the instrument. For a sample with a low concentration of particles, the size of the detection region 120 may be increased by moving the moveable lens 160 further away from the fixed lens 170, thereby increasing the beam width at the focussing lens 130. The focussing lens 130 can be adjusted to place the detection region nearer to the centre of the sample cell 110, away from the walls, so as to minimise scattering contributions from the walls.

The arrangement depicted in FIG. 3 provides for independent adjustment of the location of the detection region within the sample cell 110 (e.g. nearer or further from the wall facing the light source) and the volume of the detection region 120.

The focussing lens 130 may operate in the same way as described with reference to FIGS. 1 and 2, being moveable so as to vary the position of the focal plane 112 within the sample cell 110, and therefore to vary the position of the detection region 120.

Although the detection optical path is not shown in FIG. 3, it may be similar to that depicted in FIGS. 1 and 2, with the detection optical path passing through the focussing lens 130, so that the focus of the detection optical path is likewise moved with the focusing lens 130.

In an alternative embodiment the converging fixed lens 170 may be replaced by a diverging fixed lens. Furthermore, the moveable focussing lens 130 may be replaced by a fixed, focus tuneable lens (e.g. a deformable lens and/or a lens with tuneable refractive index).

Figure 4:
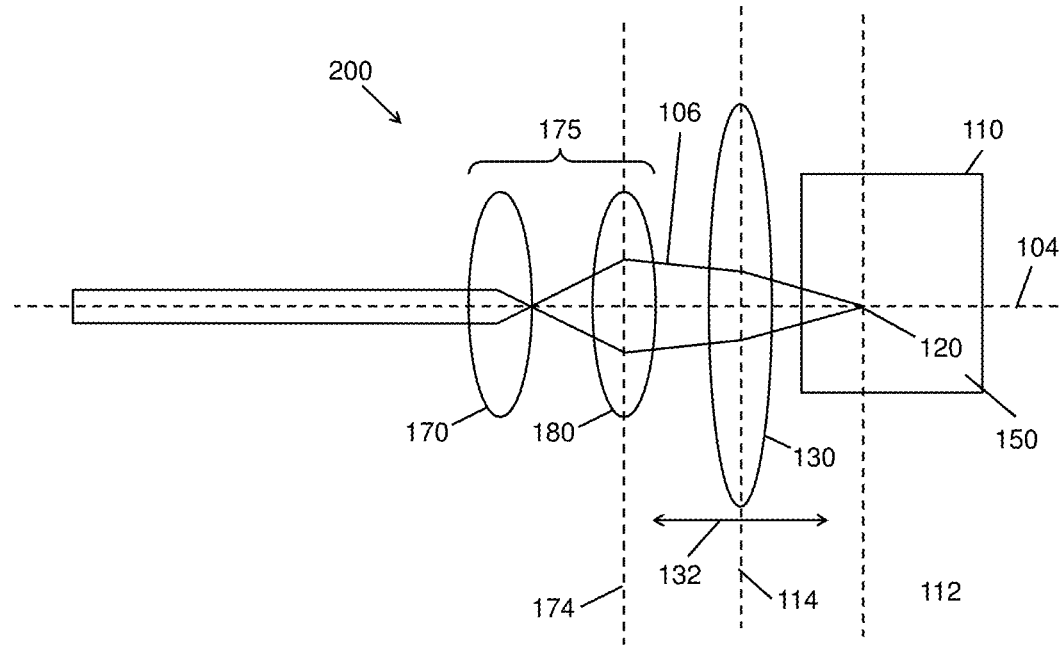
FIG. 4 is a schematic diagram of an illumination optical path in accordance with an embodiment in which a converging beam is incident on the moveable focussing lens.

Referring to FIG. 4, an alternative arrangement of an illumination optical path is shown, for use in an embodiment. The optical path comprises a beam expander 175, focussing lens 130 and sample cell 110. The focussing lens 130 and sample cell 110 may be as described with reference to FIG. 3.

The arrangement of FIG. 4 differs from that of FIG. 3 because in the arrangement of FIG. 4 the volume of the detection region 120 and the location of the detection region 120 are not independently adjustable. Instead, movement of the focussing lens 130 results in simultaneous adjustment of both the volume and location of the detection volume 120. This may be convenient, and provide a simpler arrangement with fewer moving parts.

The beam expander 175 in FIG. 4 comprises a first fixed lens 170 and a second fixed lens 180. The first fixed lens 170 is disposed between the second fixed lens 180 and the light source (not shown), and is a converging lens. The illuminating light beam 106 from the light source (which may be collimated) is incident on the first fixed lens 170. The second fixed lens 180 is positioned beyond the focal plane of the first fixed lens 170, between the first fixed lens 170 and the focussing lens 130, so the light beam 106 is diverging when it enters the second fixed lens 180. The second fixed lens 180 is arranged to produce a converging illumination beam at the moveable focussing lens 130. The width and taper of the illuminating beam 106 may be selected to provide a desired relationship between the position of the moveable focussing lens 130 (corresponding with a position of the detection region 120) and the volume of the detection region 120. In alternative arrangements, the first and second fixed lenses 170, 180 may be replaced by a single converging lens, or the first lens 170 could be a diverging lens.

Moving the focussing lens 130, closer to the beam expander 175 results in a broader beam incident on the focussing lens 130 resulting in a narrower beam waist within the sample 150 as the detection volume 120 is moved closer to the wall of the sample cell 110.

Figure 6:
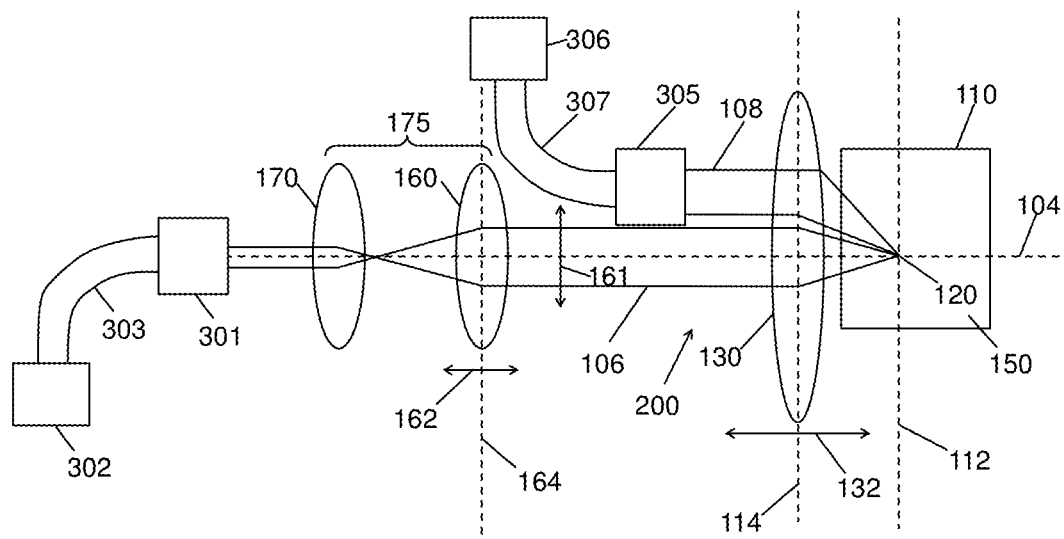
FIG. 6 is a schematic diagram of an embodiment of the invention, including the illumination optical path of FIG. 3.

Referring to FIG. 6, an example embodiment 300 is shown comprising the illumination arrangement 200 from FIG. 3. The detection optical path 108 is similar to that shown in FIGS. 1 and 2, and is focussed within the sample cell 110 by the focussing lens 130. The detection optical path 108 is coupled to a detection optical fibre 307 by a lens 305 (which may be a graded refractive index or GRIN lens). The detection optical fibre 307 couples the detection optical path 108 to the detector 306. Similarly, the light source 302 may provide illumination via an illumination optical fibre 303, via a fibre-freespace coupling lens 301 (which may be a GRIN lens).

The detector 306 may provide a signal to a processor (not shown) which may perform a dynamic light scattering analysis to characterize particles within the sample 150. A display may be provided for displaying the results of such an analysis to a user.

The illumination path, i.e. the beam 106, and the detection path 108 may pass through a common lens, i.e. the focussing lens 130 in the arrangement illustrated in FIG. 6. In alternative arrangements, the detection path 108 may pass through a separate lens from the illumination path 106, for example in order to defocus one path with respect to the other.

Figure 7:
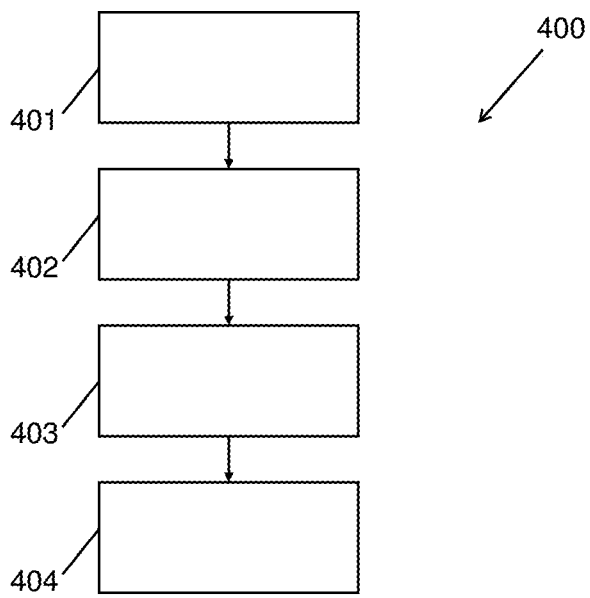
FIG. 7 is an outline flow diagram of a method of characterizing particles suspended in a sample, in accordance with an embodiment.

Referring to FIG. 7, an example method in accordance with an embodiment is shown. The method includes estimating or determining a concentration of particles within a sample 401. For instance, the concentration of particles within the fluid may be measured (e.g. by UV spectroscopy). Alternatively, the user may inspect the sample visually to determine a qualitative measure of particle concentration within the sample (e.g. to determine whether the sample appears turbid). A particle characterization instrument may be configured to automatically estimate the particle concentration (e.g. based on a scattering intensity measurement or count rate), or a user may input an estimate of particle concentration.

Following the step 401 of estimating/determining particle concentration, the location and volume of the detection region is adjusted 402, for example in response to the concentration of particles in the sample.

Once the detection region is adjusted, the detection region is illuminated, and light scattered by interactions of the illuminating beam with the sample is detected 403 (e.g. at a detector). The illumination may take place along an optical path similar to those described above. Similarly, the detection may take place along an optical path like those described above.

The data obtained by detecting the scattered light is subsequently analysed 404 in accordance with well-known dynamic light scattering techniques, so as to determine characteristics of the particles of the sample from the detected scattered light. Such analysis may be performed using a processor, and the results may be displayed on a screen or recorded on a medium (e.g. a computer readable medium).

Although example embodiments have been described in which the detection optical path is configured to detect backscattered light, in other embodiments the detection optical path may be configured to detect forward scattered light (e.g. scattered at less than 90 degrees from the illumination light beam axis 104). Furthermore, although examples have been described that use an optical fibre to couple the detector and/or the light source to the sample, it will be understood that the present invention is equally applicable to arrangements that use free space optics.

In the example embodiments a beam expander has been used to implement a variable volume detection region within the sample. However, any suitable optical assembly, optical component or components may be used to achieve this functionality. For example, a programmable or variable focal length lens may be used (e.g. having a variable refractive index or variable geometry). Alternatively, a plurality of detection paths may be used, each corresponding with a different detection volume, thereby avoiding the need to vary the width of the illuminating beam.

Embodiments have been described in which varying a beam width at the focussing lens is used to vary the detection region volume. In other embodiments, a focus tuneable lens may be used as the focussing lens, and the detection region volume may be varied by adjusting the focal length of the focus tuneable lens. The focus tuneable lens may be moveable, such that the location of the detection region can be adjusted independently of the detection region volume. In some embodiments, both a variable beam width at the focussing lens and a focus tuneable focussing lens may be used.

Figure 8:
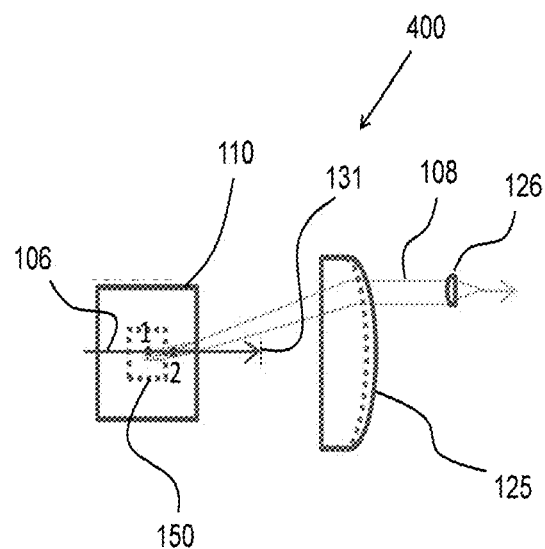
FIG. 8 is a schematic of a forward scatter detection arrangement employing a focus adjustable lens, in accordance with an embodiment.

FIG. 8 shows a detection arrangement 400 comprising a focus tuneable lens 125 (which may be a deformable lens). The illumination beam optical path 106 is incident on the sample 150 (within the sample cell 110), and light is scattered from the sample 150. After passing through the sample 150, the illumination beam is trapped at beam dump 131. Scattered light is detected in forward scatter in the example of FIG. 8. The detection optical path 108 passes through the focus tuneable lens 125, which is operable to adjust a position of the detection region within the sample 150. A fixed coupling lens 126 (e.g. a GRIN lens) may be provided to couple the detection path 108 to an optical fibre (not shown) which carries the scattered light to a detector element (e.g. photodiode).

Figure 9:
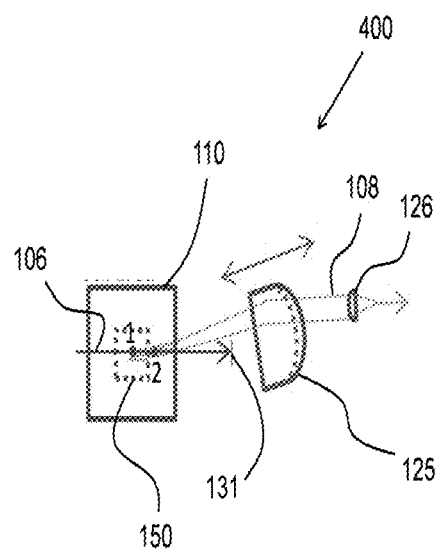
FIG. 9 is a schematic of a forward scatter detection arrangement employing a focus adjustable lens on a translation stage, in accordance with an embodiment.

FIG. 9 illustrates a further detection arrangement 400 that includes all the features of the embodiment of FIG. 8, with the exception that the focus tuneable lens 125 is mounted on a translation assembly, so that it can be moved along the detection optical path 108 to vary the distance between the sample cell 110 and the focus tuneable lens 125.

Figure 10:
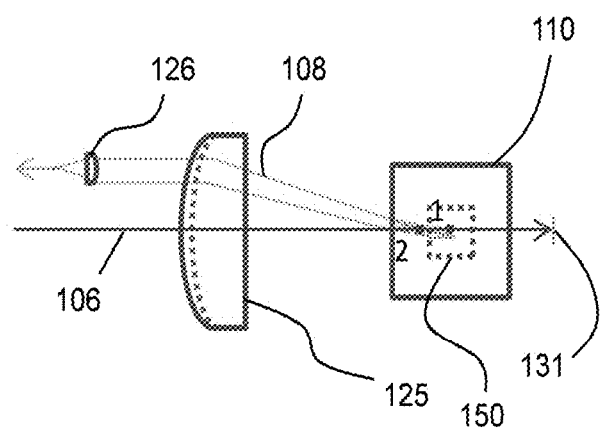
FIG. 10 is a schematic of a back scatter detection arrangement employing a focus adjustable lens, in accordance with an embodiment.

FIG. 10 illustrates an embodiment in which the illumination optical path 106 and the detection optical path 108 both pass through the focus tuneable lens 125. The illumination optical path 106 is substantially coincident with an optical axis of the focus tuneable lens 125. The detection optical path 108 is a backscatter detection path that passes through the focus tuneable lens 125 at an angle to the illumination optical path 106. Again, adjustment of the focal length of the focus tuneable lens 125 results in a change in the position of the detection region within the sample (e.g. between position 1 and position 2). The volume of the detection region may also change with adjustment of the position of the detection region, as a result of the change in the effective scattering angle of the detection optical path 108.

For instruments that seek to provide a large range of measurement types, for instance with a range of cell and sample type, concentration etc., it may be advantageous to be able to vary the intersection overlap geometry between the scattering volume and illuminating light beam and the location of the scattering volume within the sample. At present forward scattered light collection may require compensation for the difference in intersection location which occurs with different sample refractive index and different sample cell materials and geometries. It is known to compensate for such factors via a number of discrete optical flats of different thicknesses within an accessory wheel. This means a limited number of conditions can be compensated for, and there will be some level of variability in the compensation, due to tolerances in the optical flats and variations in assembly thereof. Present arrangements may also require a translation stage which may move an optical element of the collection optics. These components are presently bulky, which make it increasingly difficult to squeeze in additional capability around the cell area. By contrast, the approach of using a focus tuneable lens enables a more elegant approach, which may involve a relatively compact, single component.

In the example embodiments a focus tuneable lens 125 may be arranged to perform cell compensation for forward scattered light, and for collecting back scattered light (for example in a non-invasive back scattered light detection arrangement). Other examples are also envisaged (for example the adjustment of alternative scatter angles e.g. light scattered at 90 degrees to the illuminating light).

In FIGS. 8 to 10 intersection point '1' shows a focus tuneable lens condition that is set up to position the scattering volume at the centre of a sample cell 110 (the sample cell may be a standard 10 mm or 12 mm sample cell).

The focus tuneable lens 125 may be deformed to correct for a different cell arrangement (for example a smaller cell), or to place the scattering region nearer to (or at) the centre of a sample cell 110. This deformed configuration adjusts the location of the scattering volume to intersection point '2' by altering the focusing power from the focus tuneable lens 125. In some embodiments the focus tuneable lens 125 may not be deformed in order to adjust focus, but instead the refractive index of the lens material may be varied.

Other advantages of embodiments may include:
- A possible reduction in standoff and allowing a more "linear" optical arrangement. If the illumination beam 106 can be effectively dumped, detection closer to the illumination axis (reduced scatter angle) may be possible.
- Also different refractive indices can be continually adjusted for, opening prospects for different cell orientations, with less concern for adjustment (e.g. replicated for a 90 degree, but tilted cell arrangement).
- Characterisation of the focus adjustable lens 125 and cell 110 may mean that refractive index could be back-calculated based on drive current applied to control the focus adjustable lens.
- A symmetrical arrangement (exploiting common parts in forward and backscatter) may be advantageous. Focus adjustable lenses 125 may have a wide focus range, making a common type of focus adjustable lens applicable to collection of forward and back scattered light.
- A level of "auto-alignment" of a system would be made possible The focus adjustable lens 125 may be positioned at a distance from the sample cell 110 that is close to its minimum available stand-off range. The distance from the focus adjustable lens 125 to the sample cell 110 may be less than 40 mm, 30 mm, 20 mm, or 10 mm). This has several advantages in enabling a miniaturised optical arrangement.

The focus tuneable lens 125 may be provided on a translation assembly (as illustrated in FIG. 9). Providing the focus adjustable lens 125 on a translation assembly allows the intersection volume to be tailored according to the particular demands of a measurement. For example, some measurements (e.g. in small cells that may be used for characterizing samples with a high concentration of particles) would benefit from having a faster optics (tighter focus and collimated range), whilst others (e.g. at low concentration) might benefit from having a larger, broader intersection point at lower angle.

Some focus adjustable lenses have considerable imaging "coma". The applicant has found that such imaging "coma" may not substantially affect beam quality, compared with presently used solid singlet lens arrangements. Initial assessment of degradation in the back-propagating mode of collection that may occur for rays off-axis from the lens in some embodiments have also been promising.

The use of a focus adjustable lens 125 to perform cell compensation may differ from the prior art arrangements in that it may achieve overlap between the scattering volume and illuminating light beam by altering the angle of detection, rather than by translating the scattering volume without altering the angles of light collected therefrom. In some embodiments of the invention, the instrument may be configured to correct for such changes in the angles of scattered light collected that are collected and detected. Such correction may take account of whether the change in angle will result in a statistically significant variance in the output result.

The focus adjustable lens 125 may be used with a wedge optical element mounted on a translation stage. The wedge optical element may be on the same optical path (e.g. detection and/or illumination) as the focus adjustable lens 125. The adjustable wedge arrangement may be used to provide a continuous range of translation of the scattering volume without affecting the scattering angles.

The large range of focus travel for the some focus adjustable lenses is advantageous for future proofing designs.

Examples of a suitable focus tuneable lenses may be found at *http://www.optotune.com/publications*-2.

A range of alternative optical arrangements are envisaged, and these embodiments are merely illustrative. A deformable lens may provide additional degrees of freedom compared to previously known arrangements in which a translating lens is used. A focus tuneable lens improves the provision of a range of measurement intersection geometries and locations. The measurement intersection geometries and locations may be controlled under a single drive control, and may be controlled by a user via software.

Figure 11:
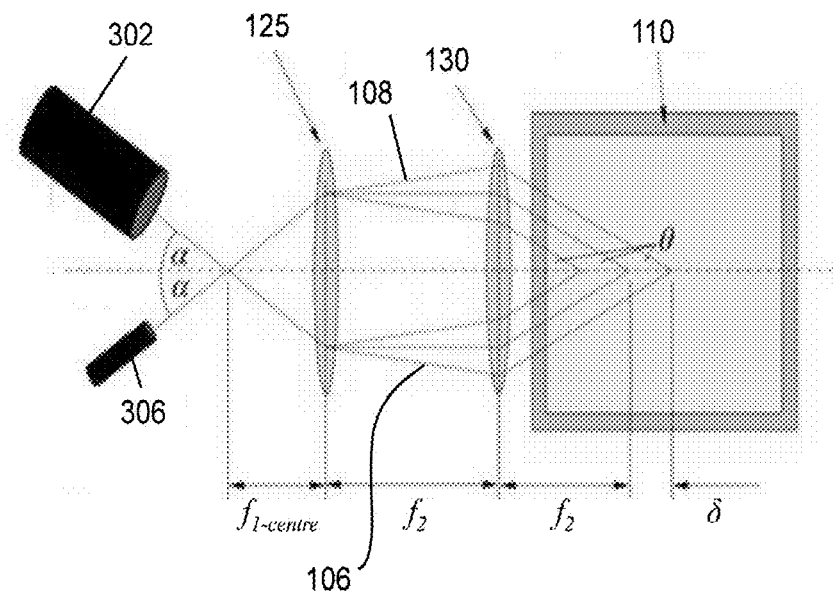
FIGS. 11 and 12 are schematics of a back scatter detection embodiment employing a focus adjustable lens in which a symmetric detection and illumination optical path is used.
Figure 12:
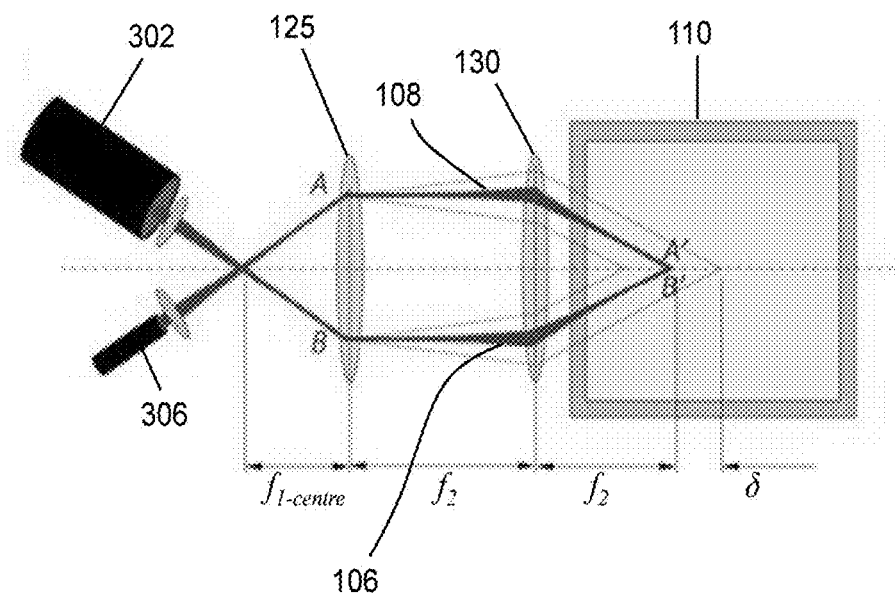

FIGS. 11 and 12 show an apparatus for particle characterisation, comprising: a light source 302, detector 306, focus tuneable lens 125, focussing lens 130, and sample cell 110.

The light source 302 is configured to illuminate the interior of the sample cell 110 with a light beam along an illumination optical path 106. The particles in the sample will scatter the illumination light beam, to produce scattered light. The detector 306 is configured to receive this scattered light along a detection path 108.

The sample cell 110 is for housing a sample (which may comprise particles suspended in a diluent medium such as water or air). The light source 302 may comprise an optical fibre that is optically coupled to a laser source. An illumination coupling lens (shown in FIG. 12) may be provided for focussing light from the light source 302 (e.g. from a fibre) onto the illumination optical path 106 at point B. The detector 306 may comprise an optical fibre that is coupled to a detection element. A detection coupling lens (shown in FIG. 12) may be provided for collecting light onto the detector 306 (e.g. coupling to a detector fibre) from a focal point A on the detection optical path 106.

The detection optical path 106 and the illumination optical path 108 are both incident on the focus tuneable lens 125 at an angle to the optical axis thereof. Each of the detection and illumination optical path 106, 108 may be at the same angle α to the optical axis. In some embodiments the optical axis of the focus tuneable lens 125, the detection optical path 108 and the illumination optical path 106 may all lie in the same plane, but this is not essential (although it may be convenient). The plane may be vertical or horizontal. The detection optical path 108 and the illumination optical path 106 may each cross the optical axis of the focus tuneable lens 125 at the back focal distance ($f_{1\text{-}centre}$) of the focus tuneable lens.

The focussing lens 130 may be a fixed focal length lens, arranged to focus the illumination and detection optical paths 106, 108 within the sample cell 110 on a detection region. The optical axes of the focus tuneable lens 125 and focussing lens 130 may be coincident.

Altering the focal length of the focus tuneable lens 125 varies the position that the illumination optical path 106 and the detection optical path 108 strike the focussing lens 130. The focus tuneable lens 125 may be placed on a back focal plane of the focussing lens 130, resulting in illumination and detection paths 106, 108 that vary in position along the optical axis of the focussing lens 130, but meet at the same detection angle θ, regardless of the focal length of the focus tuneable lens 125. This means that control of the focal length of the focus tuneable lens 125 results in a variable measurement position in the sample cell 110 at a fixed detection angle, θ.

Further, the focussing lens 130 is configured to place a conjugate image of A (the detection beam spot in the plane of the focus tuneable lens 125), at A' (within the sample cell 110) and similarly to place a conjugate image of B (the illumination beam spot in the plane of the focus tuneable lens 125) at B' (within the sample cell 110). Therefore, regardless of which path from the focus tuneable lens 125 to the optical axis is taken through the focussing lens 130, the illumination and detection paths 106, 108 will both vary in an identical manner and remain matched in size. This may be an important advantage when dealing with the number of detected coherence areas.

The symmetrical illumination of the focus tuneable lens 125 and focussing lens 130 on either side of their common optical axis ensures that the illumination and detection optical-path spot sizes are matched along the optical axis, in the sample, and that as the cross-over of illumination and detection paths moves along the optical axis, the detection angle within the sample remains constant.

The spot size will change as the focal length of the focus tuneable lens 125 is changed (varying δ), resulting in a corresponding change in the volume of the detection region. In some embodiments it may be advantageous if the smallest spot (and hence detection region) occurs at the position closest to the cuvette wall (which may correspond with a shorter focal length), as this minimises the distance between the cell wall and the detector, with advantages for concentrated samples (multiple scattering events are reduced). The detection angle θ can be any physically realisable angle but, θ<10 degrees may be advantageous as it is over this range of angles that multiply scattered light is known to have a similar relaxation time to singly scattered light, with additional advantages for samples with relatively high concentration.

Figure 13:
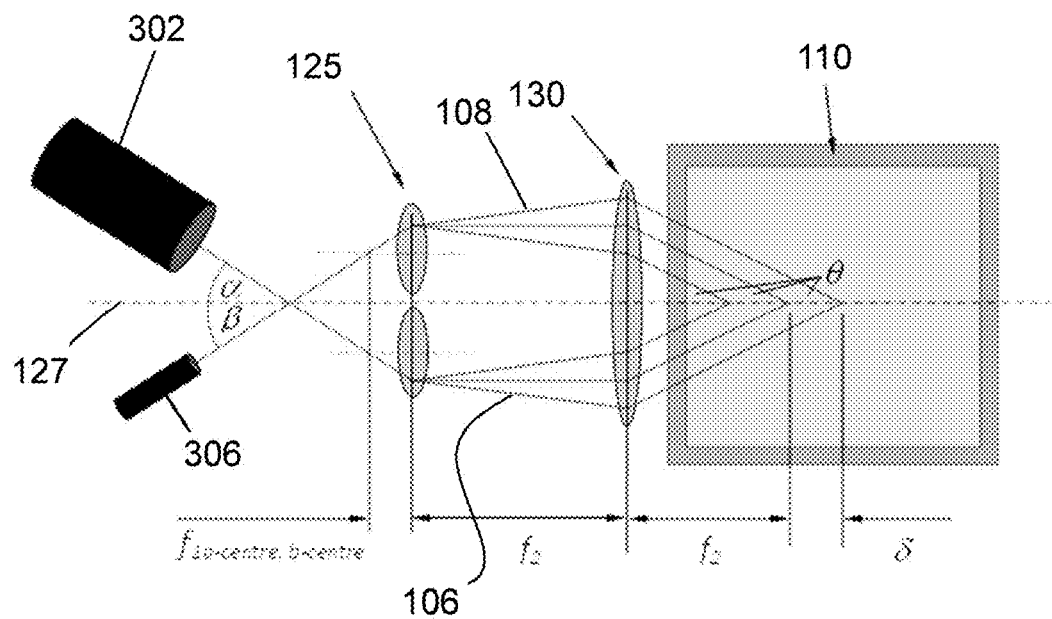
FIG. 13 is a schematic of a back scatter detection embodiment employing a focus adjustable lens in which a non-symmetric detection and illumination optical path is used, with first and second focus tuneable lens elements.

FIG. 13 illustrates an alternative embodiment, similar to that of FIG. 12, but in which the illumination and detection optical paths 106, 108 are not at the same angle to the optical axis of the focussing lens 130. In this embodiment, the illumination optical path 106 is at an angle α to the axis of the focussing lens 130, and the detection optical path is at a different angle β to the axis of the focussing lens 130. In this example the focus tuneable lens 125 comprises a first tuneable lens element on the illumination optical path 106 and a second tuneable lens element on the detection optical path 108. Each focus tuneable lens element may be arranged such that the illumination and detection optical path respectively crosses the lens element axis at the back focal distance ($f_{1a\text{-}centre}$ and $f_{1b\text{-}centre}$ respectively). This arrangement results in a constant scattering angle θ as the position of the scattering volume in the sample is varied by adjusting the focal length of the focus tuneable lens 125.

Figure 14:
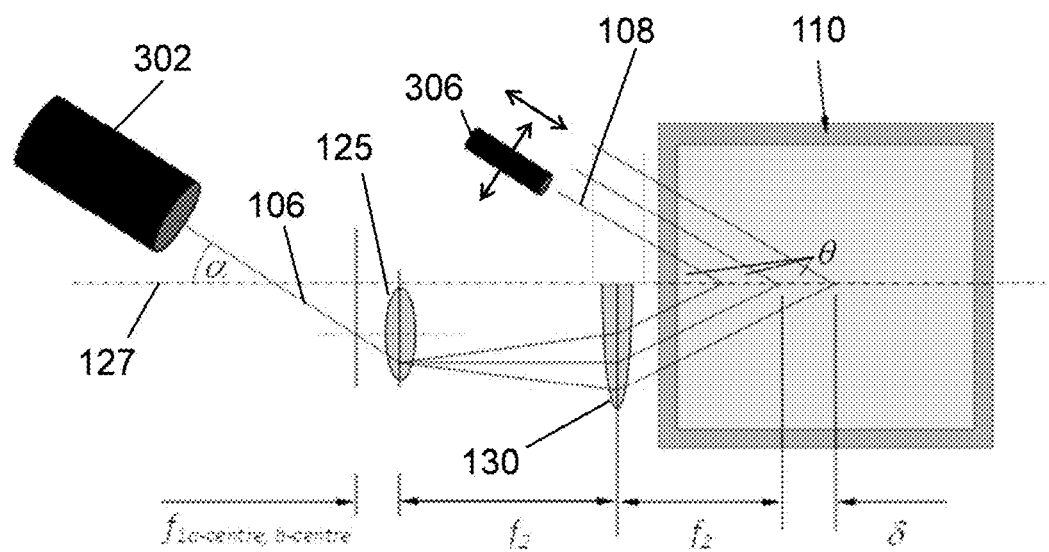
FIG. 14 is a schematic of a back scatter detection embodiment employing a focus adjustable lens in which a non-symmetric detection and illumination optical path is used, and a moveable detector is employed.

FIG. 14 shows a further alternative embodiment in which the detector 306 is moveable, and directly receives scattered light from the sample cell 110, without the scattered light passing through the focussing lens 130 or focus tuneable lens 125. The detector 306 may be moveable laterally to track the changing position of the illumination beam in the sample as the focal length of the focus tuneable lens 125 is varied, and/or may be moveable longitudinally, for example to vary a focal spot size in the sample cell.

Figure 15:
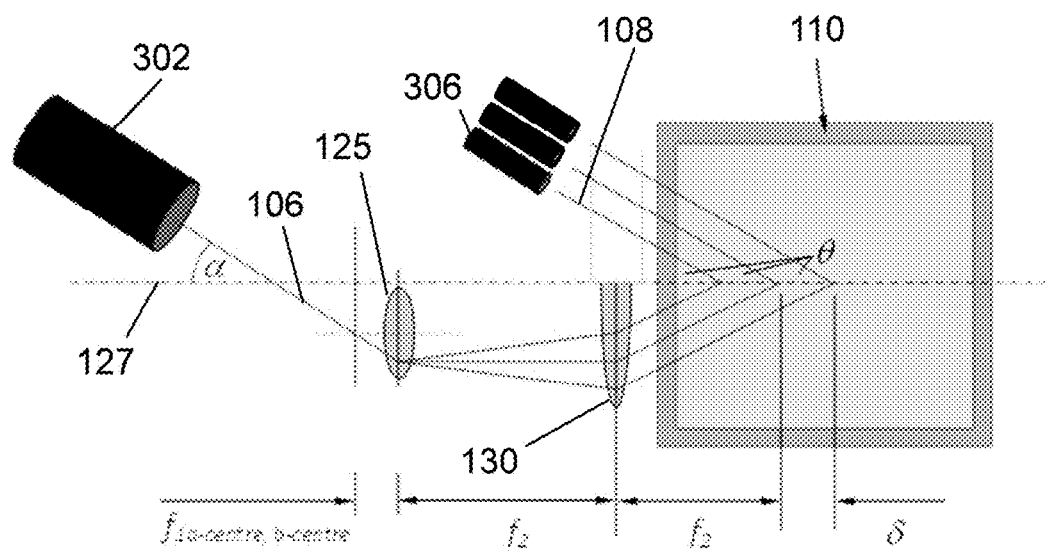
FIG. 15 is a schematic of a back scatter detection embodiment employing a focus adjustable lens in which a non-symmetric detection and illumination optical path is used, and plurality of detector fibres is employed.

FIG. 15 shows a further alternative embodiment in which the detector 306 comprises a plurality of detector fibres, arranged to receive light scattered from different locations within the sample, as a result of adjustment of the focus tuneable lens.

Figure 16:
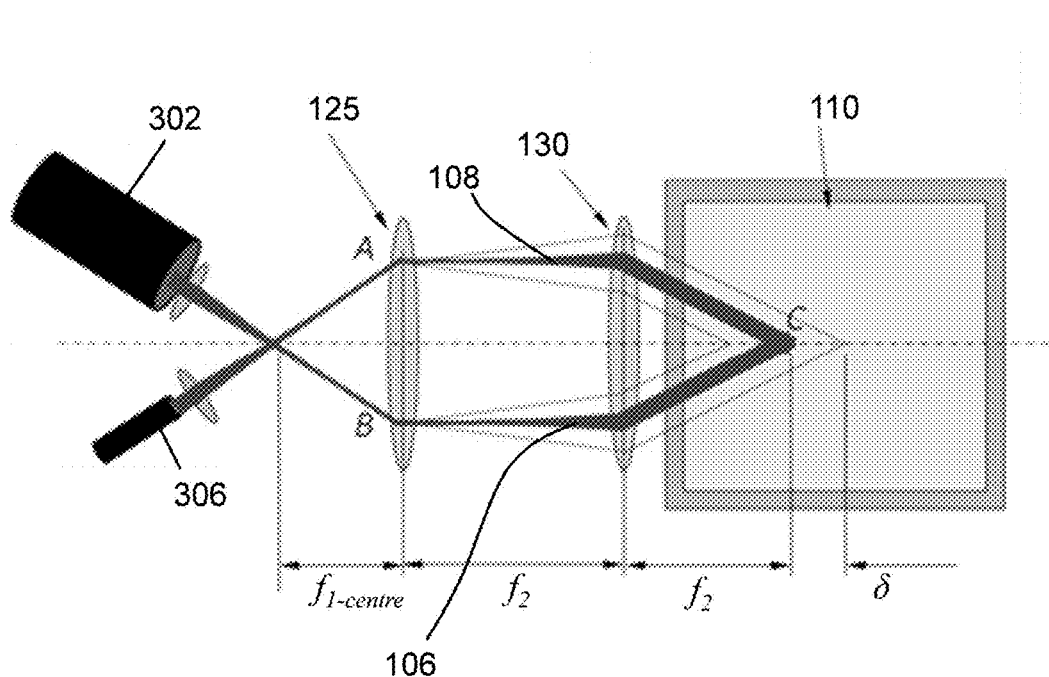
FIG. 16 is a schematic of a back scatter detection embodiment employing a focus adjustable lens in which a symmetric detection and backscatter optical path is used, and the illumination and detection beams are collimated in the sample.
Figure 17:
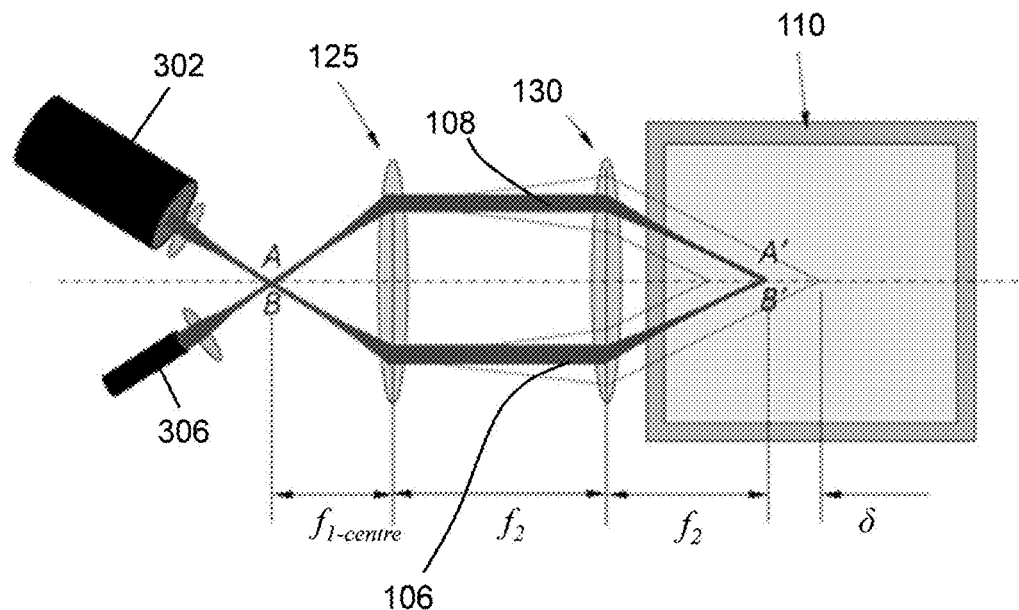
FIG. 17 is a schematic of a back scatter detection embodiment employing a focus adjustable lens in which a symmetric detection and backscatter optical path is used, and the illumination and detection beams are focussed in the sample.

The focus tuneable lens 125 and focussing lens 130 may be configured to collimate the illumination and detection optical paths 106, 108 in the sample (e.g. at C), as illustrated in FIG. 16, which otherwise has all the features of FIG. 12. In the arrangement of FIGS. 12 and 17 the detection and illumination beams are focussed (rather than collimated) in the sample by the focussing lens 130.

Figure 18:
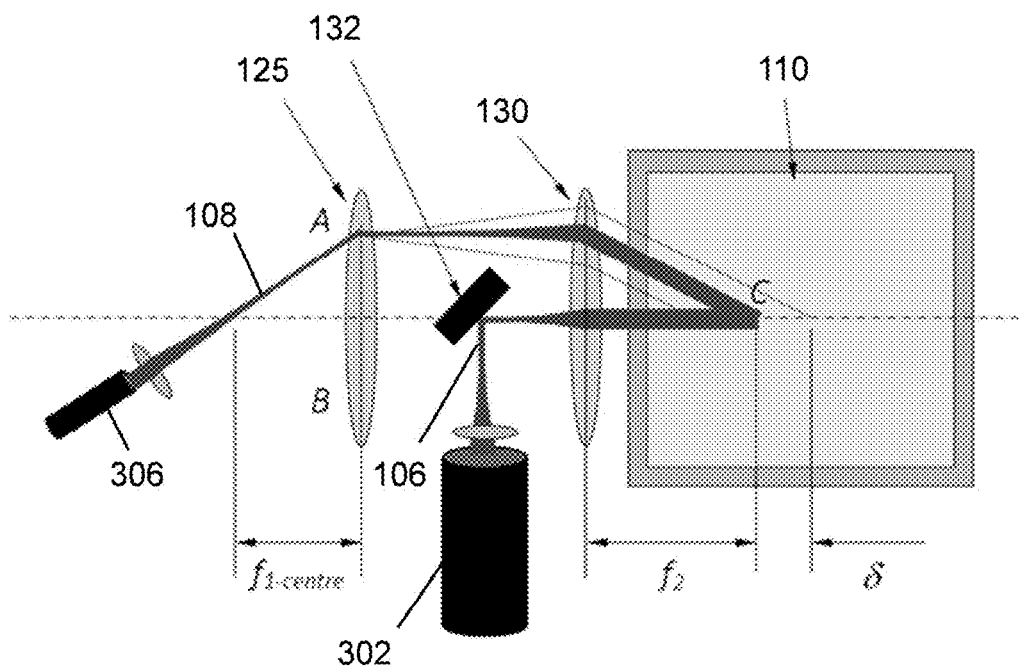
FIG. 18 is a schematic of a back scatter detection embodiment in which the illumination optical path is not symmetric with the detection optical path.

FIG. 18 illustrates an alternative backscatter detection arrangement in accordance with an embodiment, in which the detection optical path 108 has all the features described with reference to FIG. 16. The detection arrangement comprises a detector 306, focus tuneable lens 125, focussing lens 130, sample cell 110, light source 302, and illumination mirror 132.

The detector 306 comprises an optical fibre, and detects light scattering from the sample (as a result of illumination along the illumination optical path 106). A fibre coupling lens is provided to couple the detection optical path 108 to the detector fibre. The detection optical path 108 comes from the sample cell 110, through the focussing lens 130, through the focus tuneable lens 125, through the fibre coupling lens and into the detector fibre 306. The illumination optical path 106 does not pass through the focus tuneable lens 125, but is instead directed through the focussing lens 130 (e.g. along the axis of the focussing lens) by an illumination mirror 132. In the arrangement of FIG. 15 the illumination and detection paths are illustrated as collimated in the sample cell 110, but this does not have to be the case—they may be focussed within the sample cell 110 instead. Using a separate illumination optical path may simplify alignment of the detection arrangement: it may be easier to align more optical elements along a common axis.

Figure 19:
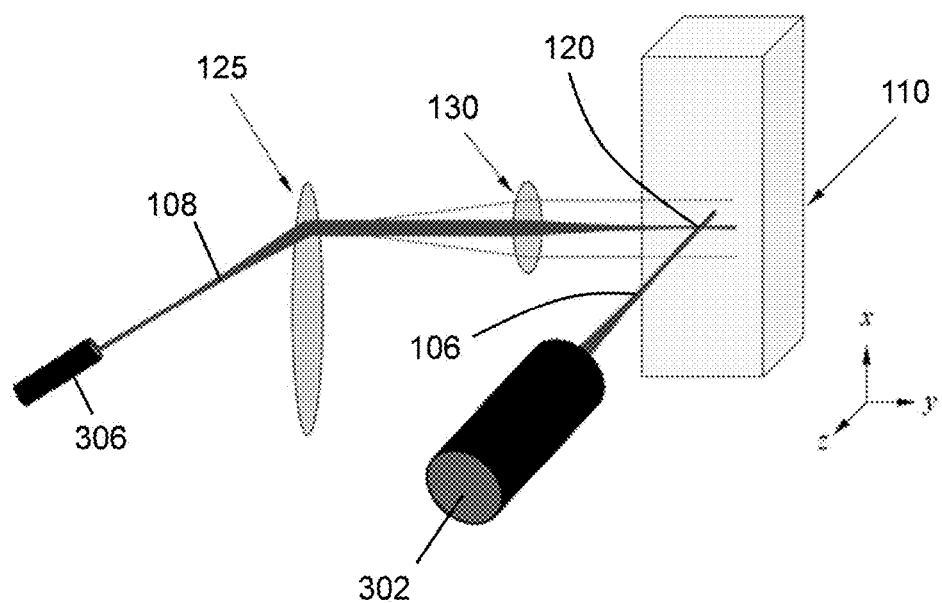
FIG. 19 is a schematic of a side scatter detection embodiment with a variable focal length lens.

FIG. 19 illustrates a side-scatter detection embodiment, in which the illumination and detection optical paths 106, 108 are at 90 degrees to each other in the sample cell 110. The detection optical path 108 passes through a focus tuneable lens 125 and a focussing lens 130, and is focussed in the sample cell 110 (although in another embodiment it could alternatively be collimated by the focussing lens 130 in the sample cell 110). The illumination optical path 106 may be focussed or collimated in the sample cell 110 by one or more lenses (not shown). The one or more lenses may comprise a fixed focal length or a focus tuneable lens.

In a side-scatter detection configuration the detection region at the overlap of the illumination optical path 106 and the detection optical path 108 tends to be very small (e.g. less than 100 μm in extent) and can therefore be sensitive to pointing stability in the light source (e.g. laser) and to optical alignment variation in the optical bed (that holds the optical elements in relative alignment), particularly in the x-direction (as shown), due to shipping, thermal variation, etc.

The focus tuneable lens 125 may be used to compensate (in at least 1 degree of freedom) for any such optical misalignment. There are cases where a collimated beam, rather than a focussed system, may be beneficial, for example for high scattering applications (e.g. turbid samples). In the example shown in FIG. 19, adjustment of the focal length of the focus tuneable lens 125 results in adjustment in x (i.e. vertical) of the detection optical path (in the sample cell 110, relative to the illumination optical path 106). In an alternative embodiment, the focus tuneable lens 125 may be configured to compensate in the z direction, parallel with the illumination optical path in the sample cell (e.g. with a detection optical path 108 in a horizontal plane instead of a vertical plane) or y direction, or may be configured for compound adjustment (of at least one of an x, y, or z position), e.g. using an focus adjustable cylindrical lens, and/or a detection optical path 108 at a compound angle to the illumination optical path 106.

Figure 20:
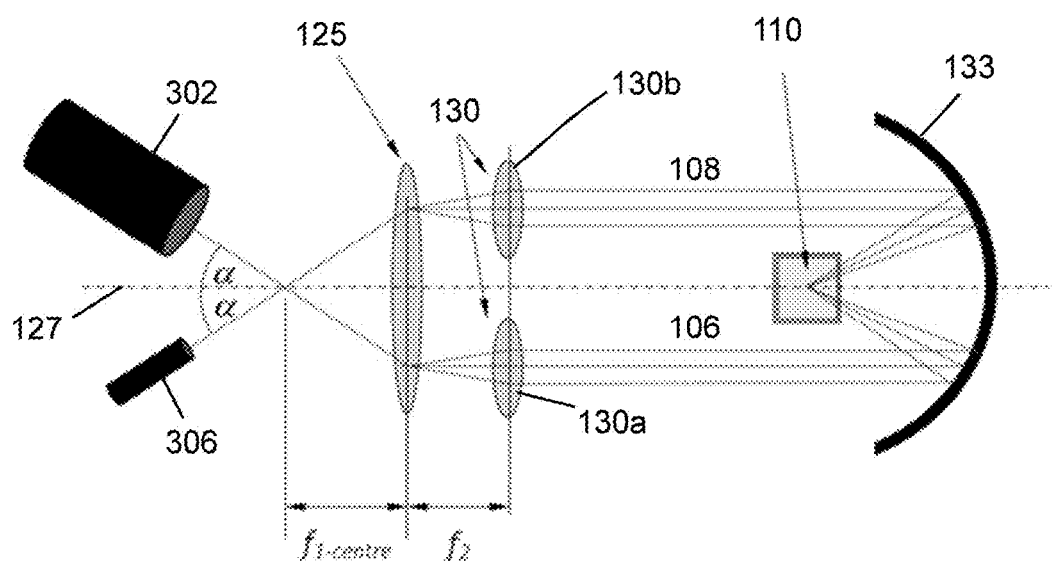
FIG. 20 is a schematic of a backscatter detection embodiment employing a curved reflector (e.g. mirror) to direct the illumination and detection optical paths into the sample carrier.

FIG. 20 shows a back scatter detection arrangement with a symmetric detection and illumination optical path 106, 108. The detection arrangement shown comprises a light source 302, detector 306, focus tuneable lens 125, focussing lenses 130, focussing reflector 133 and sample cell 110. Each of the detection and illumination optical path 106, 108 is at the same angle α to the axis of the focus tuneable lens 125 at incidence therewith. Conveniently, the detection and illumination optical paths may lie in the same plane (e.g. a horizontal or a vertical plane). In this embodiment the focussing lens 130 comprises an illumination focussing lens 130a and a detection focussing lens 130b. The focussing lens 130 directs the illumination and detection optical path 106, 108 onto the (curved) focussing mirror 133, which re-directs the illumination and detection paths 106, 108 to a detection region within the sample cell 125 (e.g. in a collimated or focussed beam). In this embodiment, the position of the detection region is not changed when the focal length of the focus adjustable lens 125 is varied. Instead the angle between the illumination optical path 106 and the detection optical path 108 within the sample is changed. When the focal length of the focus adjustable lens 125 is increased, the angle between the illumination optical path 106 and detection optical path 108 in the sample cell 110 is increased (and the converse is true).

In another embodiment the focussing mirror 133 may be replaced with a further focussing lens, placed between the focussing lens 130 and the sample cell 110. Embodiments that allow adjustment of the scattering angle (i.e. the angle between the illumination and detection optical path at the scattering volume) may be used to perform a static light scattering measurement at a plurality of measurement angles. In some embodiments a variable wavelength light source may be used, so that both wavelength and scattering angle θ can be varied (thereby enabling greater range of adjustment of the 'q' vector).

Figure 21:
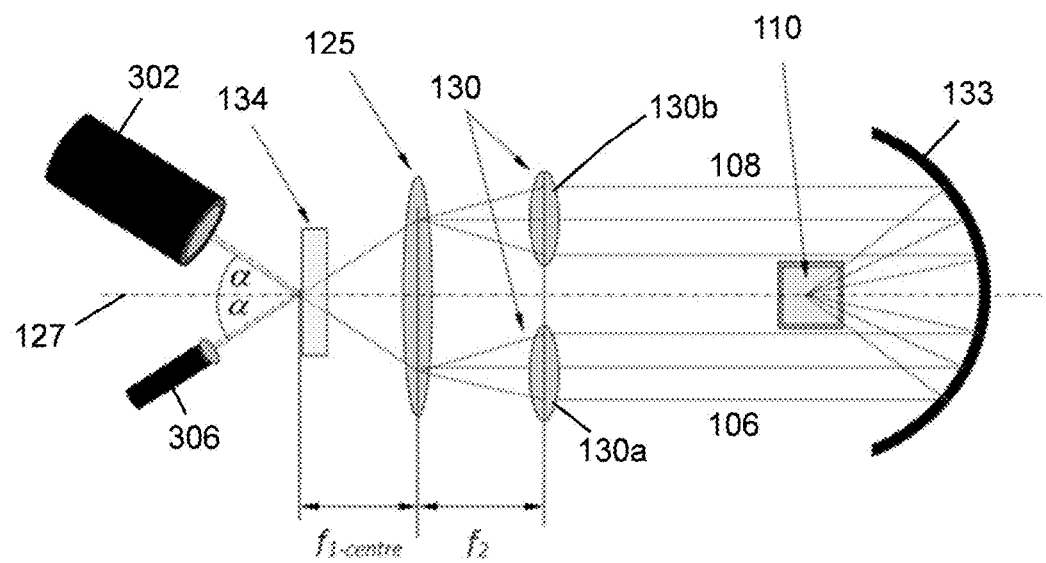
FIG. 21 is a schematic of a heterodyne backscatter detection arrangement, in which a curved mirror directs the illumination and detection optical paths into the sample carrier and a beam splitter is used to divert part of the illuminating light beam onto the sensor.

FIG. 21 shows a heterodyne back scatter arrangement, which is the same as that shown in FIG. 20, but which includes a beam splitter 134, placed at the point of intersection of the illuminating optical path 106 and the detecting optical path 108. The beam splitter 134 is configured to direct a portion of the illuminating light beam from the illumination optical path 106 to the detector 306, as a reference beam for mixing with the scattered light on the detection optical path 108, so as to perform optical heterodyning at the detector 306. A beam splitter 134 may be used in any of the other embodiments described herein (e.g. that do not include a reflector), and is not limited to this particular example.

In some embodiments, it may be useful to modulate one of the reference beam and the scattered light, for example to perform heterodyne detection of low frequency particle movement (e.g. zeta potential measurement). At least one of the optical elements in the illumination and/or detection optical path may be moveable, so as to facilitate this.

Figure 22:
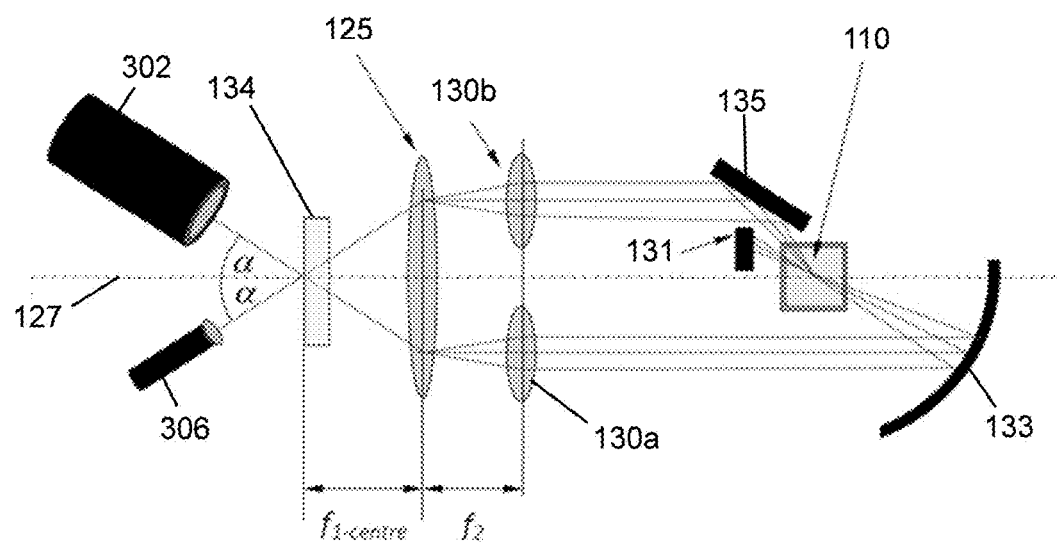
FIG. 22 is a schematic of an alternative heterodyne backscatter detection arrangement in which a plane mirror directs the detection optical path into the sample, and a curved mirror directs the illumination optical path into the sample.

An example embodiment that is suitable for modulated heterodyne detection in forward scatter is shown in FIG. 22. The illumination optical path 106 in this example is the same as shown in FIG. 21, except that the focussing mirror 133 is smaller, and is not employed in the detection optical path 108. Instead, the detection optical path 108 in FIG. 22 is configured to detect forward scatter, via plane mirror 135. The plane mirror 135 directs light scattered at a range of forward scattering angles to a focussing lens 130b, through the focus tuneable lens 125 and beam splitter 134, to the detector 306. The plane mirror 135 may be mounted on an actuator or a translation stage, operable to move/vibrate the plane mirror 135 (e.g. in a direction normal to the plane of the mirror), so as to spatially modulate the scattered light, thereby enabling modulated heterodyne detection at the detector 306. A beam dump 131 is provided to trap the illumination light beam after it has passed through the sample cell 110.

Figure 23:
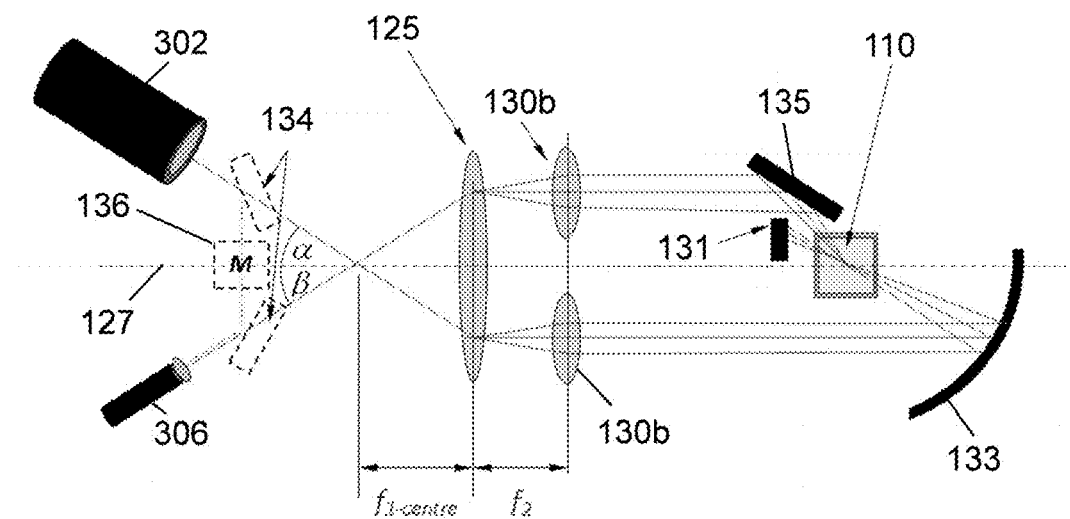
FIG. 23 is a schematic of a further alternative heterodyne backscatter detection arrangement in which a plane mirror directs the detection optical path into the sample, and a curved mirror directs the illumination optical path into the sample.

FIG. 23 shows an alternative embodiment suitable for modulated heterodyne forward scatter measurement, in which the respective angles α, β of incidence of the illumination optical path 106 and detection optical path 108 at the focus tuneable mirror 125 are different, but which is otherwise similar to the example of FIG. 22. Instead of a beam splitter at the point of intersection of the illumination and detection optical paths 106, 108, a beam splitter is provided on the illumination optical path (before the focus tuneable lens 125) and a recombiner is provided on the detection optical path to combine the reference beam with the detection optical path 108 before the detector 306. A modulator 136 is provided in the optical path of the reference beam. In some embodiments the beam splitters and modulator may be omitted.

Any appropriate element may be actuated/vibrated to provide modulation, such as the detector 306, or the focussing mirror 133.

Figure 24:
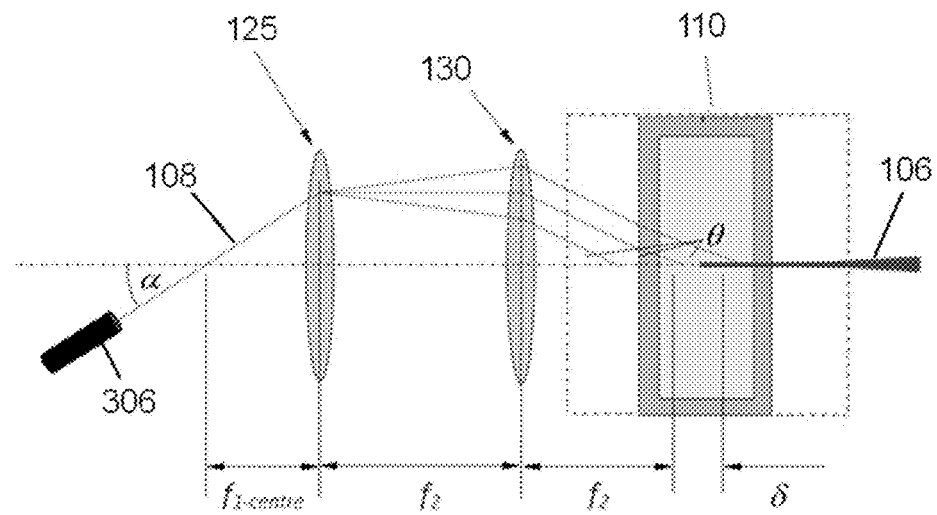
FIG. 24 is a schematic illustrating cell depth compensation in a forward scatter detection arrangement.

FIG. 24 shows an example of how a focus tuneable lens 125 may be used to compensate for different sizes and positions of sample cell 110, and/or to compensate for different sample wall refractive index and/or thickness in accordance with embodiments of the present disclosure. This example is a forward scatter detection arrangement, in which the illumination optical path 106 is only sketched to improve clarity. Any illumination optical paths can be used on conjunction with the correction described herein.

When the sample cell 110 is large in cross section, a short focal length of the focus tuneable lens 125 can be used to place the scattering volume close to the wall of the sample cell 110 (for example, when the sample is turbid). When the sample cell 110 is smaller, a longer focal length may be appropriate. Sample cells 110 with different refractive index and wall thickness will refract an angled detection optical path to a different degree, placing the scattering volume in a different position in the sample cell 110. Adjustment of the focal length of the focus tuneable lens 125 can be used to compensate for both different refractive indices and different cell wall thickness.

Figure 25:
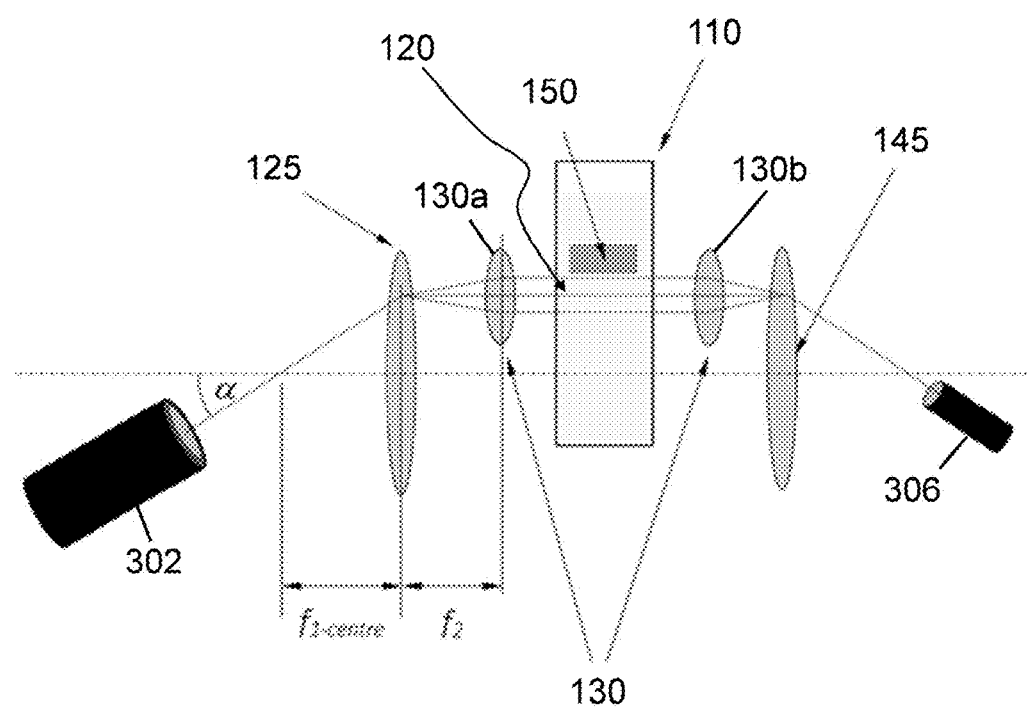
FIG. 25 is a schematic illustrating vertical alignment adjustment in a forward scatter detection arrangement.

Referring to FIG. 25, a dip cell arrangement is shown for measuring surface charge and/or electrophoretic mobility of particles suspended in a liquid, similar to that described in EP2721399. The sample cell 110 forms a measurement chamber for receiving a sample holder 150. An arrangement is provided for applying an electric field to the sample in the sample holder 150. For example, the sample holder 150 may be provided with an opposed pair of electrodes, and be configured to hold a sample in position in a measurement volume between the pair of electrodes such that a planar surface of the sample is aligned orthogonally to the electrode surfaces.

In the prior art (e.g. in EP2721399) a mechanical actuator is provided to adjust a position of the planar surface of the sample with respect to a scattering volume from which light scattered from a fixed illuminating beam is detected. The arrangement of FIG. 25 illustrates how a focus tuneable lens 125, 145 can be used to vary the relative positions of the planar surface of the sample and the scattering volume 120 (e.g. to change how close the scattering volume is to the planar surface).

In the example of FIG. 25 the light source 302 illuminates the scattering volume 120 via a focus tuneable lens 125. The light source 302 is incident on the focus tuneable lens 125 at an angle α to the axis of the focus tuneable lens 125, and the focus tuneable lens 125 refracts the illumination optical path to illuminate a location within the sample cell. A focussing lens 130a is provided between the focus tuneable lens 125 and the sample cell 110, for example to collimate or focus the illuminating light beam within the sample cell 110. The detection optical path may be symmetric with the illumination optical path about the sample cell, having a corresponding further focus tuneable lens 145 and focussing lens 130b. Adjustment of the focal length of the focus tuneable lenses 125, 145 has the effect of changing the position of the scattering volume 120 within the sample cell 110 (e.g. in the vertical direction). The measurement of surface charge can be more easily automated with such an arrangement, since there is no longer a need to adjust a mechanical actuator and physically move the sample holder with respect to the illumination optical path.

Using the optical schemes disclosed herein, it is possible to use a variable focus lens to move the position of coincidence of the illumination and detection path into a single-mode, few-mode, multi-mode fibre, or a pinhole entrance aperture to another optical detection layout. This allows non-invasive backscatter detection to be implemented without any moving parts, significantly reducing wear over the lifetime of a particle characterisation instrument and allowing the possibility of modulating the measurement position at high frequency, (e.g. greater than 20 Hz), for instance for time resolved positional studies.

A number of other applications exist for embodiments which facilitate re-positioning of the detection region. A concentration gradient (e.g. a vertical concentration gradient) may be determined by taking a plurality of measurements at different locations. The speed of repositioning of a focus tuneable lens may be faster than slewing a conventional optical element, enabling such analysis to occur more rapidly. Gel domain locations can be explored (in at least one of x, y and z directions), for example to investigate different rheological domains using DLS.

In some embodiments it may be possible to reposition an illumination or detection optical path to avoid a mark or surface inclusion on a low quality sample cell. Such a defect will generally result in a high count rate and a low intercept in the correlogram. If these features are present in the data and/or the correlogram, the apparatus may be configured to try a different measurement location and/or to seek a measurement location with a more optimal count rate and correlogram intercept (by varying the focal length of the focus tuneable lens).

In embodiments which facilitate adjustment of the detection optical path relative to the illumination optical path (e.g. as shown in FIG. 19) it may be possible to increase the dynamic range of an instrument to accommodate more strongly scattering samples without saturation of the detector by deliberately misaligning the illumination and detection optical path. This may be simpler and more elegant than including attenuation filters in the illumination and/or scattering optical paths.

It will be understood that features of each example can be combined with those of other examples. For example, in the embodiment of FIG. 25, a fibre array or a moving detection arrangement (similar to that shown in FIGS. 14 and 15) could be used instead of the focus tuneable lens 145.

Other variations and modifications will be apparent to the skilled person, and are intended to be within the scope of the invention, which is defined by the appended claims.

The invention claimed is:

1. A particle characterisation apparatus for performing a static light scattering measurement or a dynamic light scattering measurement, comprising:
   a light source for illuminating a sample with a light beam;
   a detector arranged to detect scattered light from the interaction of the light beam with the sample;
   a focus tuneable lens arranged to collect the scattered light for the detector from a scattering volume and/or to direct the light beam into the sample, wherein the focus tuneable lens comprises a deformable lens or a material in which a refractive index may be varied by application of a stimulus, and the focus tuneable lens adjusts a location of the scattering volume by changing the focal length of the focus tuneable lens; and a focussing lens between the focus tuneable lens and the sample, wherein a focal point of the focussing lens is coincident with a principle plane of the focus tuneable lens.

2. The apparatus of claim 1, wherein the apparatus is arranged so that adjustment of the focal length of the focus tuneable lens results in a change in the location of the scattering volume without a change in the angle between the illumination and detection optical paths.

3. The apparatus of claim 1, comprising a detection optical path, by which the scattered light reaches the detector, and an illumination optical path, by which the light beam reaches the sample from the light source, wherein the detection optical path and/or the illumination optical path pass through the focus tuneable lens.

4. The apparatus of claim 3, wherein: the focus tuneable lens has an optical axis; the detection optical path is at a first, non-zero, angle to the optical axis; the illumination optical path is at a second, non-zero, angle to the optical axis.

5. The apparatus of claim 4, wherein the first angle and second angle are substantially equal.

6. The apparatus of claim 4 wherein the first angle and/or second angle is 10 degrees or less.

7. The apparatus of claim 3, wherein the detection optical path and illumination optical path cross at a first location at a distance from the focus tuneable lens, the first location being on the optical axis of the focus tuneable lens and between the light source and the focus tuneable lens.

8. The apparatus of claim 7, wherein the focus tuneable lens is operable to have a focal length that co-locates a focal point of the focus tuneable lens with the first location, wherein the focus tuneable lens is un-powered when the focal point is co-located with the first location.

9. The apparatus of claim 1, wherein moving the position of the scattering volume in the sample closer to the light source by changing the focal length of the focus tuneable lens results in a decrease in the scattering volume, and moving the position of the scattering volume in the sample further from the light source by changing the focal length of the focus tuneable lens results in an increase in the scattering volume.

10. The apparatus of claim 1, wherein the apparatus comprises a sample holder with an opposed pair of electrodes, the sample holder configured to hold a sample in position in a measurement volume between the pair of electrodes such that a planar surface of the sample is aligned orthogonally to the electrode surfaces, the planar surface adjacent to the scattering volume, and wherein adjustment of the focal length of the focus tuneable lens results in adjustment of the relative position of the planar surface and scattering volume by moving the scattering volume.

11. The apparatus of claim 1, wherein the focus tuneable lens is operable to compensate for at least one of: a refractive index of the sample, an orientation of a sample cell within which the sample is held, a refractive index of the sample cell and the geometry of the sample cell.

12. The apparatus of claim 1, wherein the focus tuneable lens is mounted on a translation stage.

13. The apparatus of claim 1, wherein the focus tuneable lens is arranged to collect at least one of forward scattered light, back scattered light and side scattered light.

14. The apparatus of claim 1, wherein the light beam passes through the focus tuneable lens.

15. The apparatus of claim 1, wherein the detector comprises a detector optical fibre with an end for receiving scattered light, the end of the detector optical fibre being mounted on a translation stage.

16. A method of performing a dynamic or static light scattering measurement, comprising:
 illuminating the sample with a light beam, thereby producing scattered light by the interaction of the light beam with the sample;
 detecting scattered light along a detection optical path that intersects the light beam within the sample at a detection region, thereby obtaining data;
 adjusting at least one of a location of the detection region, a volume of the detection region, or an angle between the illumination and detection optical path at the detection region, by changing the focal length of a focus tuneable lens in at least one of the illumination and detection optical path, wherein the focus tuneable lens comprises a deformable lens or a material in which a refractive index may be varied by application of a stimulus and between the focus tuneable lens and the sample is a focusing lens, wherein a focal point of the focusing lens is coincident with a principle plane of the focus tuneable lens;
 repeating, at least once, the step of detecting scattered light after performing at least one corresponding step of adjustment by changing the focal length of the focus tuneable lens;
 performing a static or dynamic light scattering measurement using the data obtained from at least one focal length of the focus tuneable lens.

17. The method of claim 16, comprising performing a dynamic light scattering measurement, in which each adjusting step changes at least a position of the detection region, and each adjusting step is in response to measurement data corresponding with a preceding adjustment step.

18. The method of claim 17, comprising performing a dynamic or static light scattering measurement by obtaining measurement data from a plurality of scattering angles by adjusting the focal length of the focus tuneable lens.

* * * * *